(12) United States Patent
Tang et al.

(10) Patent No.: US 9,554,946 B2
(45) Date of Patent: Jan. 31, 2017

(54) WOUND PROTECTING AND FIXING DEVICE

(76) Inventors: Erhu Tang, Guangzhou (CN); Yina Tang, Guangzhou (CN); Qiongchen Jiang, Guangzhou (CN)

( * ) Notice: Subject to any disclaimer, the term of this patent is extended or adjusted under 35 U.S.C. 154(b) by 137 days.

(21) Appl. No.: 14/363,080

(22) PCT Filed: Feb. 16, 2012

(86) PCT No.: PCT/CN2012/071199
§ 371 (c)(1),
(2), (4) Date: Aug. 12, 2014

(87) PCT Pub. No.: WO2013/082883
PCT Pub. Date: Jun. 13, 2013

(65) Prior Publication Data
US 2015/0025436 A1    Jan. 22, 2015

(30) Foreign Application Priority Data

Dec. 7, 2011   (CN) .......................... 2011 1 0403898

(51) Int. Cl.
*A61F 13/02*    (2006.01)
*A61M 25/02*    (2006.01)
*A61F 13/00*    (2006.01)

(52) U.S. Cl.
CPC ....... *A61F 13/0243* (2013.01); *A61F 13/0226* (2013.01); *A61F 13/0246* (2013.01);
(Continued)

(58) Field of Classification Search
CPC ....................................................... A61F 13/00
(Continued)

(56) References Cited

U.S. PATENT DOCUMENTS

| 697,637 A | * | 4/1902 | Lee ............................... 128/888 |
| 1,920,808 A | | 8/1933 | Eugen |

(Continued)

FOREIGN PATENT DOCUMENTS

| CN | 201088670 Y | 7/2008 |
| EP | 0507459 A1 | 10/1992 |

(Continued)

OTHER PUBLICATIONS

China Patent Office, "Notice to grant an invention patent for CN 201104038983," Jan. 16, 2014.

(Continued)

*Primary Examiner* — Tarla Patel
(74) *Attorney, Agent, or Firm* — Manabu Kanesaka

(57) ABSTRACT

A wound protecting and fixing device includes at least a protecting and fixing layer (1) with an opening. The opening (11) is defined in the protecting and fixing layer and configured to extend between an upper plane and a lower plane of the protecting and fixing layer along a longitudinal direction, and to surround a wound therein so that the protecting and fixing layer (1) with the opening limits an increase of tension at the wound and a movement-incurred wrinkle of skin at the wound. The protecting and fixing layer (1) with the opening includes a flexible protecting and fixing layer (1*a*) with an opening and a rigid protecting and fixing layer (1*b*) with an opening. The device can prevent the wound from being ripped and ruptured, and prevent damages caused by movement-incurred wrinkles of the skin at the wound and relative displacement frictions.

20 Claims, 13 Drawing Sheets

(52) U.S. Cl.
CPC ..... *A61M 25/02* (2013.01); *A61F 2013/0028* (2013.01); *A61F 2013/0057* (2013.01); *A61F 2013/00412* (2013.01); *A61M 2025/0273* (2013.01)

(58) Field of Classification Search
USPC ........... 602/41–43, 54, 57–60; 128/888–889; 215/235, 237; 220/254.3; 222/556
See application file for complete search history.

(56) References Cited

U.S. PATENT DOCUMENTS

| | | | |
|---|---|---|---|
| 2,367,690 A * | 1/1945 | Purdy | 128/888 |
| 4,890,608 A * | 1/1990 | Steer | 602/57 |
| 5,086,763 A | 2/1992 | Hathman | |
| 5,447,492 A * | 9/1995 | Cartmell et al. | 602/58 |
| 5,520,629 A | 5/1996 | Heinecke et al. | |
| 5,562,107 A | 10/1996 | Lavender et al. | |
| 5,686,096 A | 11/1997 | Khan et al. | |
| 5,693,068 A | 12/1997 | Kuhlman | |
| 5,702,356 A * | 12/1997 | Hathman | 602/41 |
| 6,124,520 A | 9/2000 | Roberts | |
| 6,550,646 B1 * | 4/2003 | Takahara et al. | 222/107 |
| 7,265,256 B2 * | 9/2007 | Artenstein | 602/42 |
| 7,344,512 B2 | 3/2008 | Yamazaki et al. | |
| 7,723,561 B2 * | 5/2010 | Propp | 602/58 |
| 7,816,577 B2 | 10/2010 | Aali | |
| 8,252,971 B2 | 8/2012 | Aali et al. | |
| 8,328,858 B2 * | 12/2012 | Barsky et al. | 607/90 |
| 8,708,982 B2 * | 4/2014 | Lin | 604/307 |
| 2004/0138602 A1 | 7/2004 | Rossen | 602/41 |
| 2007/0161937 A1 | 7/2007 | Aali | |
| 2008/0033377 A1 * | 2/2008 | Kauth et al. | 604/304 |
| 2010/0256545 A1 * | 10/2010 | Aali et al. | 602/43 |
| 2012/0046582 A1 * | 2/2012 | Hopman et al. | 602/4 |

FOREIGN PATENT DOCUMENTS

| | | |
|---|---|---|
| EP | 1344539 A2 | 9/2003 |
| JP | H08-33674 A | 2/1996 |
| JP | H09-182801 A | 7/1997 |
| WO | 90/05558 A1 | 5/1990 |
| WO | 2004/041064 A2 | 5/2004 |
| WO | 2011/008360 A1 | 1/2011 |

OTHER PUBLICATIONS

China Patent Office, "First Office Action for CN 201104038983," Oct. 16, 2012.
China Patent Office, "Response to First Office Action for CN 201104038983," Feb. 28, 2013.
China Patent Office, "Second Office Action for CN 201104038983," Jun. 20, 2013.
China Patent Office, "Response to Second Office Action for CN 201104038983."
China Patent Office, "Opinion Statement for CN 201104038983," Dec. 20, 2013.
Japan Patent Office, "Office Action for Japanese Patent Application No. 2014-545061," Nov. 4, 2014.
Japan Patent Office, "Office Action for Japanese Patent Application No. 2014-545061," Apr. 14, 2015.
Japan Patent Office, "Notice of Allowance for Japanese Patent Application No. 2014-545061," Jul. 7, 2015.
Australia Patent Office, "Patent Examination Report No. 1 for Australian Patent Application No. 2012350078," Sep. 17, 2014.
Australia Patent Office, "Patent Examination Report No. 2 for Australian Patent Application No. 2012350078," Aug. 20, 2015.
Australia Patent Office, "Notice of Acceptance for Australian Patent Application No. 2012350078," Sep. 1, 2015.
Europe Patent Office, "Extended Search Report for European Patent Application No. 12855779.0," Mar. 6, 2015.
Europe Patent Office, "Supplementary Search Report for European Patent Application No. 12855779.0," Mar. 24, 2015.
Europe Patent Office, "Exam Report for European Patent Application No. 12855779.0," Oct. 26, 2015.
Europe Patent Office, "Examination Report for European Patent Application No. 12855779.0," May 9, 2016.

* cited by examiner

WOUND PROTECTING AND FIXING DEVICE

CROSS-REFERENCE TO RELATED APPLICATIONS

This application claims the benefit of International PCT Application No. PCT/CN2012/071199, filed on Feb. 16, 2012, which claims the benefit of Chinese Patent Application No. 201110403898.3 filed on Dec. 7, 2011, now Chinese Patent No. CN 102429769B; the contents of which are hereby incorporated by reference.

FIELD OF THE PATENT APPLICATION

The present patent application relates to the field of medical assistive devices and technologies, and more specifically to a wound protecting and fixing device.

BACKGROUND

In people's lives, due to harms caused by many factors, the human body may incur wounds such as external injury wounds, surgical wounds, infusion wounds, and so on. A wound, once incurred, must be protected and tended so that severe complications caused by wound infections can be prevented. Hence excellent wound protection and care technologies and products are critically important to expedite the healing of wounds. Currently in clinical medicine, a wound is protected and tended mainly through wound dressings. Such products mainly include spunlace non-woven cloths, transparent thin film dressings, foam dressings, hydrocolloid dressings, functional dressings, and etc. To achieve better results, different types of dressings are used to protect and tend different types of wounds. If the protecting and tending methods, technologies and products are inappropriate, the damages to the wound will be aggravated. Therefore, attention should be paid to the wound damage aggravation caused by current wound protecting and tending technologies and products during protecting and tending wounds, or the failure of achieving optimal protecting and tending effects caused by functional defects of the products. To create new products with better healing effects, based on the characteristics of wounds to be tended, a simple categorization of the wounds is made, while advantages and disadvantages of the conventional technologies and products in protecting and tending the wounds are analyzed and compared.

The first type of wounds is that with infusion catheters. In tending this type of wounds, such as wounds with central venous catheters, peripherally inserted central catheters, and vein retaining needle catheters, besides that the catheter must be securely fixed, the wound needs to be specially protected to prevent infection, and in some cases, the catheter needs to be retained for as long as a few months so as to cure the disease. Currently a clinically preferred method is to use transparent thin film dressing (PU film) to directly cover the infusion wound and fix the catheter, with the advantages of:

1. The dressing being super thin and transparent, so that the wound development status can be observed any time;
2. Excellent flexibility and conformability with the skin. Once the dressing is affixed to the skin, it is hard to separate the dressing and the skin.

Therefore, compared with dressings made of other materials, such dressing is more secure and less likely to fall off in fixing the catheter and protecting the infusion wound.

However, the dressing has the following disadvantages:

1. Because of its good flexibility, along with a movement-incurred wrinkle of the superficial skin, the dressing will generate the same movement-incurred wrinkle and not be able to prevent the movement-incurred wrinkle of the skin. As a result, when the superficial skin generates a movement-incurred wrinkle under an external force or caused by a body movement, the catheter will have a displacement thereby damaging the infusion wound;
2. The adhesive is sealed on the infusion wound, which may cause allergy at the wound or skin around the wound and generate inflammatory responses such as contact dermatitis;
3. The dressing is not sweat permeable, so that sweat may accumulate at the wound or under the thin film, which may easily cause wound infections, even secondary severe complications such as phlebitis, or bloodstream infection;
4. The dressing needs to be changed in 3 to 6 days. Not changing the dressing and subsequently sanitizing the wound for a period longer than that may cause infection.

The second type of wounds are regular wounds such as surgical wounds, external injury wounds and etc. Clinically this type of wounds are normally handled by using spunlace non-woven cloths with pads or cushions, foam dressings, hydrocolloid dressings and so on to tend and protect the wounds. This type of dressings have the following advantages:

1. The dressings have strong absorbency. They can absorb wound exudation and prevent the expansion of the infection area.
2. There is no adhesive in direct contact with the wound.
3. The hydrocolloid dressings can keep the wound tissues moist and expedite the healing.

However, such dressings have the following disadvantages:

1. The dressings are not transparent (the hydrocolloid is translucent), as a result, the development status of the wound cannot be observed any time.
2. Compared with transparent thin film dressings, such dressings have weaker flexibility and conformability, and stronger hardness and rigidity. Under tension, the dressing can easily fall off from the surface of the skin, thereby having lower fixity. When the dressing is conformed to wounds at movable joint parts of the body where movement-incurred wrinkles may easily be generated, or when the patient is sweating as a result of movement, the dressing may easily fall off.
3. The dressings have bad waterproofness, or is not waterproof at all. The adhesive layer of the dressing may easily fall off from the skin when being in contact with water.
4. When the superficial skin of the wound has a movement-incurred wrinkle, there may be friction caused by relative displacement between the superficial skin of the wound and the pad or cushion as well as the dressing that the wound directly contacts, so that further damage may be caused to the wound tissues, especially for wounds at movable joint parts of the body.

In addition, the above-mentioned dressings are in direct contact with and pressingly covered upon the wound, and therefore may conglutinate with the secretion of the wound tissue. When the dressing is changed, further damage may be caused to the wound tissue. Although non-conglutination technical processing is applied to the part of the dressing which contacts the wound, but the non-conglutination is only relative. At the same time, when a sanitization processing is made to the wound from time to time, all of the above-mentioned dressings have to be changed as a whole.

In addition to the above-mentioned technologies, currently, some dressings that prevent tissue adherence or "non-contact" wound protecting and tending devices such as "covers", "frames" and other wound protecting and tending technologies, have appeared, but these anti-tissue-adherence materials can not completely prevent tissue adherence, or tissue rejection and inflammatory reactions against the foreign bodies. In addition, the wound protecting and tending devices such as the "covers" and the "frames" have complex structures. Lacking an effective fixing method, such devices are hard to be stably fixed and may easily move so as to cause further damages to the wound. Such devices cannot be applied to the fixation of central venous catheters, peripherally inserted central catheters, and vein retaining needle catheters, or to the protecting and tending of infusion wounds. Furthermore, the manufacture and application of such devices are relatively complicated. Hence it is difficult to widely promote the application of such devices clinically.

In addition to the above-mentioned disadvantages of the conventional technologies and methods for wound protecting and tending, the conventional technologies and methods cannot prevent the wound from being ripped and ruptured under an external force or tension. Currently, there are no clinically effective methods or technologies to address wound ripping and rupture, especially for surgical wounds and external injury wounds at the abdomen and movable joint parts. Ripping and rupture caused by coughing, postoperative abdominal distension, forcibly urination and defecation, and so on, may severely affect the wound healing and cause complications such as infection.

Whether the adhesion between a wound protecting and tending product and the surface of the skin is secure is also an important factor that determines the effect of wound protecting and tending. Therefore, the physiological characteristics of the human superficial skin determine and influence the effects of the wound protecting and tending product. The human skin has the following physiological characteristics:

1. The skin is an organ that secretes sweat. The sweat being secreted will reduce the adhesiveness of the protecting and fixing adhesive layer, and even make it fall off;

2. The skin has a relatively soft surface, which moves and produces wrinkles along its texture under an external force, especially at joint parts with movement functions. The older the age, more wrinkles there are, and more easily the wrinkles may be produced. Therefore, when a rigid protecting and fixing adhesive layer that can relatively hardly wrinkle or cannot wrinkle adheres to the surface of the skin, and when the adhering surface undergoes a tension produced by movement-incurred wrinkles being created under an external force, it will first resist the tension of the movement-incurred wrinkles so as to limit the displacement and the wrinkling of the surface of the skin. When the adhering force is not enough to resist the tension, the adhering surface will peel and fall off. Therefore, when only using the rigid fixing adhesive layer to bond and secure an object on the surface of the skin, the advantage is that it can resist the tension of the movement-incurred wrinkles of the skin so as to limit the movement-incurred wrinkles on the adhering surface or the surface of the skin surrounded by the opening thereof. However, the disadvantage is because it requires the adhering force with the skin to resist the tension of the movement-incurred wrinkles of the skin, when the adhering force is not enough to resist the tension of the movement-incurred wrinkles of the skin, or when the tension with the adhesive surface of the skin increases, the rigid protecting and fixing adhesive layer will peel and fall off. On the other hand, when a flexible protecting and fixing adhesive layer adheres to the surface of the skin, because it is soft, ultra-thin, and has good conformability, it may generate the same movement-incurred wrinkles as the movement-incurred wrinkles of the skin textures, and keep a good adherent state with the skin under any movement-incurred wrinkle conditions. Hence, the tension of the movement-incurred wrinkles of the skin is not against the adhering force. When using a flexible protecting and fixing adhesive layer to protect and fix medical items or wounds at the surface of the skin, the advantage of it is that the adhesion is tight and secure, and even when there is sweat, it will not fall off easily. The disadvantage of it is that the medical items or the wound that the protecting and fixing adhesive layer is protecting and fixing generates displacements and movement-incurred wrinkles along with the movement-incurred wrinkles of the surface of the skin. For a catheter fixture with an infusion opening or a fixture with wound dressing, the catheter at the infusion opening will move while the surface of the wound will generate movement-incurred wrinkle. As a result, further damage will be caused to the wound while the relative displacement frictions between the wound and the dressing will do harm to the wound tissue.

3. Skin wounds of allergic constitution will be allergic to the adhesive layer, which leads to inflammation and infection. Hence it is necessary to avoid the adhesive layer directly adhering to infusion wounds, surgical wounds and traumatic wounds.

Therefore, considering the advantages and disadvantages of the above-mentioned methods and products being applied to wound protecting and tending, according to the physiological characteristics of the skin, it is necessary to develop a new method or product that inherits and integrates the advantages of the conventional technologies and overcomes the disadvantages, and to create a new adhering, protecting and fixing method and product that suit the physiological characteristics of the skin. The improved technologies, methods or products should meet the following requirements:

1. being capable of effectively preventing wounds (including surgical stitching wounds, traumatic wounds, infusion wounds and some high tension wounds) from being ripped and ruptured;

2. being capable of contacting the wound secretion in a permeating mode, instead of tightly and pressingly contacting the wound secretion, so that the product can effectively absorb the secretion liquid of the necrotic tissues of the wound and prevent regional spreading, with no or very little conglutination with the wound tissue;

3. being capable of letting the wound be open and visible so that the developing status of the wound can be observed any time;

4. being capable of securely fixing and adhering to skin around the wound and fixing the infusion catheter, just as using transparent thin film dressings alone, without being bonded to wounds or infusion wounds by the adhesives, while being transparent and visible at the same time;

5. being capable of limiting further damages to the wound caused by the movement-incurred wrinkles of the superficial skin of the wound and the displacement of the catheter, especially for wounds and infusion wounds at movable joint body parts or with relatively many skin wrinkles;

6. based on the requirements of the wound characteristics, being capable of completely preventing the wound surface from contacting any foreign body (including the dressing itself) so as to prevent the wound from having foreign body rejection and inflammation responses;

7. if needed, debridement, sanitization, drainage, and regional medical and physical treatment may be conducted to the wound without changing the wound protecting and tending product as a whole;

8. while protecting the wound, being capable of securely fixing the catheter related to the wound so that the catheter may not easily fall off, just as using the transparent thin film dressing alone, preventing the displacement of the catheter on the surface of the skin when using the transparent thin film dressing alone, and preventing the infusion wound from being damaged by catheter displacement.

9. if needed, being waterproof, air permissible and capable of keeping away the contaminations from the external environment;

10. being capable of lowering the frequency of changing wound care products so as to reduce medical costs.

SUMMARY

An object of the present patent application is to provide a wound protecting and fixing device to improve the protecting and fixing effect for surgical wounds, traumatic wounds and infusion wounds, facilitate wound healing, and ensure the effect of clinical treatment.

To solve the above problems, the present patent application provides: a wound protecting and fixing device including at least a protecting and fixing layer with an opening; wherein the opening is configured to extend between an upper plane and a lower plane of the protecting and fixing layer along a longitudinal direction throughout the protecting and fixing layer, and to surround a wound therein so that the protecting and fixing layer with the opening limits an increase of tension at the wound and a movement-incurred wrinkle of skin at the wound.

In this technical solution, the opening surrounds the surgical wound, the external injury wound and the infusion wound inside itself so that the protecting and fixing layer with the opening limits an increase of tension at the wound and a movement-incurred wrinkle of skin at the wound, prevents wound ripping and rupturing, and prevents damages being done to the wound caused by movement-incurred wrinkles of the wound skin and relative displacement frictions between the wound, the dressing and the catheter, thereby improving the effects of protecting the wound and infusion wound, facilitating wound healing, effectively preventing infusion wound infection, and ensuring the effect of clinical treatment, especially for high tension surgical wounds at the abdomen, wounds at movable joint parts of the body, and patients who needs long term infusion therapy through venous catheters. In this technical solution, a cavity is formed in the protecting and fixing layer with the opening. Through adjusting the thickness of the protecting and fixing layer with the opening, or the height or volume of the cavity, the dressing covering the wound contacts the wound secretion in a permeating mode, and absorbs oozed liquid of the wound, preventing further damages to the wound resulted from allergic responses caused by adhesives contact and conglutination between the dressing and the wound secretion caused by using dressings to press and contact the wound and by directly bonding infusion wounds in the conventional technologies, and keeping the wound and the infusion wound in an opening cavity where they cannot be touched by any foreign object (including the dressing) so as to prevent contact inflammation from happening.

The protecting and fixing layer with the opening is made of or partially made of transparent thin film materials (PU film), which is transparent, waterproof, air permeable, and with good flexibility and conformability. The characteristics of this material are: the material can generate the same movement-incurred wrinkles as the wrinkles that the texture of the skin generates, remain good flexibility and conformingly and securely adhere to the wound, the skin around the infusion wound, and the catheter being covered so that itself as well as the catheter cannot be easily separated and falling off from the surface of the skin. It can also bond other adhering objects to the surface of itself more securely. In addition, the fastness of this structure is much stronger than directly bonding to the skin. Covers such as plastic, silicon gel, foam, hydrocolloid, non-woven cloth, and so on, make it not easy for the whole fixing layer to be separated and falling off from the surface of the skin. The fixing is more secure, thereby protecting the wound and infusion wound more effectively.

The protecting and fixing layer with the opening is or partially is made of materials such as silicon gel, plastic, foam, hydrocolloid, multi-layer compressed thickened non-woven cloth, and etc. Comparing with transparent thin films (PU film), this material has relatively stronger rigidity with the characteristics of: the material does not generate movement-incurred wrinkles as the skin it adheres to wrinkles with its texture, and can effectively limit the wound surrounded by the opening and the cavity formed by the opening, the movement-incurred wrinkles of the superficial skin at the infusion wound during body movement or under the pulling of an external force, and the increase of tension at the wound, thereby preventing wound ripping and rupture, preventing damages done to the wound by movement-incurred wrinkles of the wound, and the relative displacement friction between the wound and the dressing, limiting the movement-incurred wrinkles caused by the catheter being bonded, the surface of the skin and other protecting layers, and preventing the catheter from moving and damaging the wound.

Preferably, the protecting and fixing layer with the opening includes a flexible protecting and fixing layer with an opening and a rigid protecting and fixing layer with an opening. A cavity is defined in the rigid protecting and fixing layer with the opening. In this technical solution, because the protecting and fixing layers with openings of different material characteristics are used, the respective characteristics of protecting and fixing the wound are expressed. The flexible protecting and fixing layer with the opening, with a characteristic of being ultra-thin, after being bonded to the skin, may generate the same movement-incurred wrinkles as the superficial skin wrinkles with its texture, and preferably is made of transparent thin film (PU film). The rigid protecting and fixing layer with the opening, compared with the flexible protecting and fixing layer with the opening, is more rigid and thicker. After being bonded to the surface of the skin, it does not generate the same movement-incurred wrinkles as the superficial skin wrinkles with its texture, and does not generate wrinkles. The materials for it may be chosen based on different wound characteristics, which may be a soft material to satisfy the comfort of the skin, or may be a hard, inelastic, hard-to-deform material, such as plastic, silicon gel, foam, hydrocolloid, non-woven cloth, and etc., as long as it does not generate the same movement-incurred wrinkles as the superficial skin wrinkles with its texture after being bonded to the skin. When the skin to which the flexible protecting and fixing layer with the opening is bonded generates movement-incurred wrinkles under an external force, almost no tension is produced at the adhesive surface between the flexible protecting and fixing layer with the opening and the skin. Therefore, no matter how the skin generates movement-incurred wrinkles, sweats or soaks in water, the flexible protecting and fixing layer with the opening will not separate from the surface of the skin and fall off. When the rigid protecting and fixing layer with the opening is bonded to the surface of the skin, the rigid protecting and fixing layer with the opening will resist the tension produced by the skin wrinkles and deformation, limit the skin wrinkles, and when the displacement force of the movement-incurred wrinkles of the skin is greater than the adhesive force that the rigid protecting and fixing layer with the opening staying on the skin generates, the rigid flexible protecting and fixing layer with the opening will be separated and fall off, which is more easily to happen when the skin sweats or soaks in water. However, when the rigid protecting and fixing layer with the opening adheres to the flexible protecting and fixing layer with the opening that has been bonded to the skin, the adhesive force is greatly enhanced and sufficient to resist the tension produced at the adhesive surface by the movement-incurred wrinkles of the flexible protecting and fixing layer with the opening and the skin so that the rigid protecting and fixing layer with the opening will not separate and fall off from the surface of the flexible protecting and fixing layer with the opening, and not affect the secure adherence between the flexible protecting and fixing layer with the opening and the surface of the skin. At the same time, the rigid protecting and fixing layer with the opening can limit the movement-incurred wrinkles of the flexible protecting and fixing layer with the opening adhering thereto, the movement of medical items being fixed, and the movement-incurred wrinkles of the skin of the surface of the wound surrounded by the opening, thereby preventing damages from being done to the skin by the movement-incurred wrinkles of the skin of the surface of the wound, limiting the increase of tension at the wound, preventing wound ripping and rupturing, and prevent damages being done to the infusion wound by the displacement of the catheter. In addition, because the outer boundary of the flexible protecting and fixing layer with the opening is always larger than the outer boundary of the rigid protecting and fixing layer with the opening, the outer boundary adhering to the skin is the flexible protecting and fixing layer, so that it generates the same movement-incurred wrinkles as the superficial skin wrinkles with its texture. While the same wrinkles are produced, it will not separate, peel or fall off. Therefore, by cooperatively bonding the flexible protecting and fixing layer with the opening and the rigid protecting and fixing layer with the opening and using them to protect and fix wound and catheters, they will be very securely fixed and not easy to separate and fall off from the skin, and will be very stable and not easy to produce movement. It will securely and stably fix the whole wound protecting and fixing device to the skin around the wound so that the optimum effect of protecting the wound is achieved, and the requirements of wound care and medical items (eg. catheters) fixation are satisfied. In this technical solution, because a cavity is formed inside the rigid flexible protecting and fixing layer with the opening, by setting up different thickness of the rigid protecting and fixing layer with the opening or different height and volume of the cavity, only surface contact in a permeating mode between secretion at the surface of the wound and the covering dressing is set to be allowed to facilitate the absorption of the wound discharge, which also keeps the surface of the wound from being contacted or pressed by any foreign object (including dressing and other covering objects), prevents damages from being imposed to the wound by the relative displacement frictions between the wound and the covering dressing or the protecting and fixing layer, and prevents, further damages from being done to the wound by adhesive contacting allergic responses and conglutination between the dressing and the wound secretion caused by using dressing to press and contact the wound and directly bonding infusion wounds as in the conventional technology.

Preferably, an adhesive layer is disposed on a surface of the protecting and fixing layer with the opening. Through the adhesive layer, the protecting and fixing layer with the opening is fixed on the surface of the skin around the wound or around the infusion wound, and the protecting and fixing layers are bonded and fixed with each other.

Preferably, the flexible protecting and fixing layer with the opening is configured to follow the movement-incurred wrinkles of the texture of the superficial skin that the flexible protecting and fixing layer adheres to and produce the same movement-incurred wrinkles. The rigid protecting and fixing layer with the opening is configured to limit the movement-incurred wrinkles of the skin it adheres to, movement-incurred wrinkles of the flexible protecting and fixing layer with the opening, the wound rupture surrounded by the opening, and the movement-incurred wrinkles of the superficial skin of the wound. As a result, the flexible protecting and fixing layer with the opening does not separate and fall off from the surface of the skin under the pulling of the tension caused by the skin movement, and is securely fixed. The rigid protecting and fixing layer with the opening can limit the movement-incurred wrinkles of the skin and the flexible protecting and fixing layer with the opening it adheres to, and the movement-incurred wrinkles of the wound rupture and the superficial skin of the wound surrounded by the opening. Therefore, it can limit the increase of the tension at the wound, prevent the wound from being ripped and ruptured, prevent damage being done to the wound by the movement-incurred wrinkles of the superficial skin of the wound, prevent damage being done to the wound by the relative displacement between the wound and the covering dressing or the protecting and fixing layer, prevent damage being done to the infusion wound by the displacement of the catheter. By cooperatively bonding the flexible protecting and fixing layer with the opening and the rigid flexible protecting and fixing layer with the opening, the whole wound protecting and fixing device does not easily fall apart from the skin or produce displacement, and medical items being fixed such as central venous catheters, peripherally inserted central catheters, and vein retaining needle catheters, wound drainage tube, dialysis catheter and etc. will not move, thereby effectively protecting and fixing wounds and securely fixing all types of medical catheters.

Preferably, the flexible protecting and fixing layer and the rigid protecting and fixing layer are bonded together and aligned by the openings.

Preferably, a protecting and fixing layer with a pad and/or a protecting and fixing layer without a pad are/is disposed above the protecting and fixing layer with the opening. Such protecting and fixing layers may be made of transparent, non-transparent, flexible and/or rigid materials, and are configured to close the opening and fix or further fix the protecting and fixing layer with the opening onto the skin around the wound. The pad is configured to absorb the oozed liquid at the wound.

Preferably, a closing and opening member is disposed at the protecting and fixing layer with the opening. The closing and opening member is configured to open or close the opening.

Preferably, a pad is disposed on the lower surface of the closing and opening member and configured to be accommodated by the opening. The pad may be any type of functional pad, such as a highly absorbent pad, antiseptic pad, moisturizing pad and etc.

Preferably, the closing and opening member is detachably fixed with the protecting and fixing layer with the opening. Such configuration makes it convenient to open and close the opening repeatedly and for a doctor to treat the wound any time according to the situation of the wound.

Preferably, the closing and opening member includes a protruding wing disposed at an edge thereof. The configuration of the protruding wing makes it more convenient to exert force to pull the closing and opening member so as to save effort and time in using the device.

Preferably, a passage connecting the cavity to the outside is defined in the rigid protecting and fixing layer with the opening, the passage being configured to allow an object to enter or exit the cavity. The passage is configured to allow medical catheters such as central venous catheters and wound drainage tubes to pass through.

Preferably, a longitudinal cross-section of the rigid protecting and fixing layer with the opening has a trapezoid shape. The configuration in this technical solution makes other dressing and/or covering objects better cover and bond the protecting and fixing layer to the skin around the wound so as to achieve the optimum effect of conformity and fixture.

Preferably, the flexible protecting and fixing layer with the opening is disposed below or above the rigid protecting and fixing layer with the opening, an outer boundary of the flexible protecting and fixing layer being extending beyond an outer boundary of the rigid protecting and fixing layer. When the flexible protecting and fixing layer is disposed below the rigid protecting and fixing layer and at the surface of the skin at the wound, the rigid protecting and fixing layer with the opening is directly bonded to the top of the flexible protecting and fixing layer with the opening. Such configuration is secure and stable, making it not easy to fall apart, and not able to move, and making the items to be stably and securely fixed. Because the outer boundary of the flexible protecting and fixing layer with the opening extends beyond the outer boundary of the rigid protecting and fixing layer with the opening, the whole protecting and fixing layer will not peel off, or fall apart due to sweat and water soaking Preferably, a U shaped cut is defined at an outer edge of the protecting and fixing layer with the opening. Through the configured U shaped cut, the fixing layer more effectively fixes medical tubes such as vein retaining needle catheters, drainage catheters, and etc. through the adhesive layer.

Preferably, the wound protecting and fixing device further includes a supporting member. The supporting member is fixed with at least an upper portion of the protecting and fixing layer with the opening. The supporting member is configured to maintain and support the covering dressing, closing and opening member and other covering objects at the opening, so that they will not deform or collapse.

Preferably, the supporting member is a supporting bar, a supporting chip, a supporting block, or a supporting frame.

Preferably, the protecting and fixing layer with the opening is a combination of multiple layers of different materials. The combination can include highly absorbent materials, antiseptic materials, moisturizing materials, and materials carrying iodophor. Different functional materials can be configured according to the requirements so that an aseptic, antiseptic, growth promoting, or healing promoting internal environment is formed in the cavity of the protecting and fixing layer with the opening.

Preferably, an outer edge of the protecting and fixing layer with the opening is connected to the opening through a slit. Through the slit, the opening or the cavity may surround the infusion wound above the skin and under the catheter, and make the upper surface of the protecting and fixing layer with the opening work as a supporting pad of the catheter.

Comparing with the conventional technology, the present patent application configures at least a protecting and fixing layer with an opening, which protects and fixes the wound and the infusion wound in an opening that limits the increase of tension and movement-incurred wrinkles of the superficial skin of the wound, preventing the wound from being ripped and ruptured, preventing the damage from being caused to the wound by movement-incurred wrinkles of the skin at the wound and the relative displacement between the wound and the dressing or the catheter, filling the blanks of the conventional technology. In addition, through adjusting the thickness of the protecting and fixing layer with the opening or the height and volume of the cavity, the absorbing dressing being covered or other covering objects contact the secretion at the wound surface in a permeating mode, or the wound is kept in a state in which no foreign object can contact the wound, effectively overcoming the problems of regional skin allergy, sweat accumulation at the infusion wound under the thin film, and etc., when using the transparent thin film dressing including allergenic adhesives to directly bond and cover the infusion wound of the central venous catheter as in the conventional technologies, and thereby preventing the inflammatory response, lowering the possibility of the complication of catheter-related bloodstream infections (CRBSI) after the vessel catheter is placed, preventing regional blood circulation obstruction caused by using the cover or frame with small contact area as provided in the conventional technologies to directly press the skin around the wound; preventing the adhesives from contacting the wound and the skin around the wound so as to reduce the occurrence of skin allergic responses, and preventing foreign body rejection and blood circulation obstruction around the wound caused by directly contacting and pressing the wound, according to the requirements for patients with allergic constitution; and effectively preventing further damage from being done to the wound by conglutination between the dressing and the wound secretion.

Further, the protecting and fixing layer with the opening includes a flexible protecting and fixing layer with an opening and a rigid protecting and fixing layer with an opening. The flexible protecting and fixing layer with the opening is configured to follow the movement-incurred wrinkles the skin generate along its texture and generate the same movement-incurred wrinkles, while the rigid protecting and fixing layer with the opening is configured to limit the movement-incurred wrinkles of the skin it adheres to, of the flexible protecting and fixing layer with the opening, and of the superficial skin at the wound surrounded by the opening or cavity, and the increase of tension at the wound, thereby preventing the wound from being ripped and ruptured. By combining and using protecting and fixing layers of two different material characteristics, the advantages are kept and the disadvantages are overcome. Therefore, compared with the conventional technologies, this technology enables device to be securely fixed onto the skin around the wound, not easily fall apart, and also keep the device and the objects to be fixed such as the catheters and the dressings from moving on the skin, thereby effectively overcoming the problem of the catheter damaging the infusion wound caused by movement-incurred wrinkles of the skin or the catheter being pulled by the tension when solely using a flexible protecting and fixing layer such as a transparent thin film (PU film) to protect and fix an infusion wound as in the conventional technology, and effectively overcoming the problem of the protecting and fixing layer falling apart from the skin around the wound caused by situations such as skin tension, sweat, water soaking and etc., when solely using a rigid fixing layer dressing such as non-woven cloth, foam, and etc. to fix the wound and infusion wound as in the conventional technologies. At the same time, this technology also overcomes the disadvantages of lacking an effective fixing method and the structure being complex for wound protecting and fixing devices such as the cover or frame in the conventional technologies.

Further, a closing and opening member that can be repeatedly opened and closed is disposed on the protecting and fixing layer with the opening. The closing and opening member is configured to open or close the opening or the cavity. Such structure makes it convenient for a medical or nursing staff to treat the wound or infusion wound, such as debridement, repeat sanitization, drainage, and applying antiseptic and growth promoting medicines to the wound without changing the whole protecting and fixing device. Therefore, such protecting device can be used for a long time and the medical cost is saved.

Further, the closing and opening member is made of transparent materials so that the wound and the infusion wound are transparent and visible, and the medical and nursing staff or the patient himself can observe the developing status of the wound and the infusion wound any time without opening the closing and opening member.

Further, the protecting and fixing layer with the opening is a combination of multiple layers of different materials. Different materials have different functionalities and play different roles in protecting the wound, enhancing the effect of protection. For example, a cavity formed by a protecting and fixing layer with an opening that carries iodophor can provide an antiseptic environment to the wound and its periphery. A cavity formed by a protecting and fixing layer with an opening that carries hydrocolloid can provide a moisture environment to the wound so as to facilitate its growth and healing.

Further, because of the opening or/and passage that can be opened and closed in the technical solution, through the opening or passage that can be opened and closed, treatment such as debridement, drainage, regional medication, regional physical treatment, nutritional treatment, growth factor treatment, negative pressure treatment, and etc. can be applied to the wounds and infusion wounds that require different treatment methods, while a specific healing facilitating environment can be created for wounds of different characteristics, such as aerobic, anaerobic, dry, moist, sterile, and antiseptic environments, so as to facilitate fast healing of the wound.

BRIEF DESCRIPTIONS OF THE DRAWINGS

Figure 1:
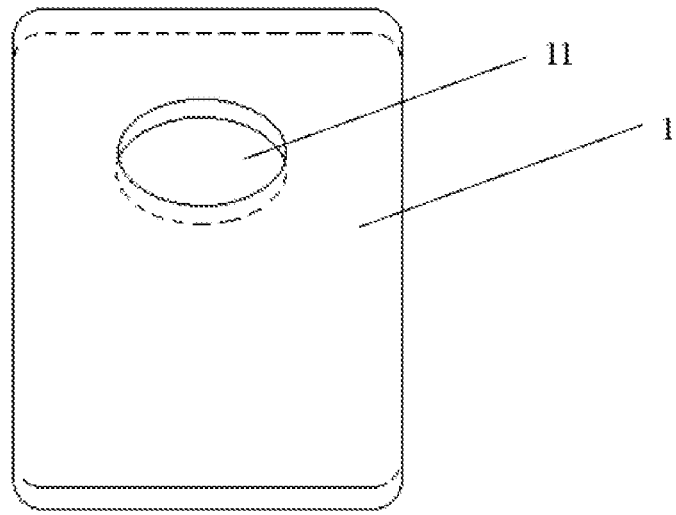
FIG. 1 is an illustrative diagram of a wound protecting and fixing device in accordance with Embodiment 1 of the present patent application.

In the drawings, the drawing marks are the following:
1: protecting and fixing layer with an opening
11: opening
12: U shaped cut
13: passage
1a: flexible protecting and fixing layer with an opening
1b: rigid protecting and fixing layer with an opening
1c: groove
1d: slit
2: closing and opening member
21: protruding wing
22: pad
3: flexible protecting and fixing layer
31: pad
4: rigid protecting and fixing layer
41: pad
42: protruding wing
5: supporting member
A: catheter
B: wound

DETAILED DESCRIPTION

The basic idea of the present patent application is to provide a wound protecting and fixing device. Through configuring a protecting and fixing layer with an opening, the opening being defined in the protecting and fixing layer and configured to extend between an upper plane and a lower plane of the protecting and fixing layer, a wound or an infusion wound being surrounded by the opening or inside a cavity formed by the opening, the following objectives and functions are achieved:

1. Through the protecting and fixing layer with the opening, the opening or the cavity is used to protect and fix the wound so that the protecting and fixing layer with the opening limits an increase of tension at the wound and a movement-incurred wrinkle of the superficial skin at the wound, thereby preventing wound ripping and rupturing.

2. The protecting and fixing layer with the opening limits a movement-incurred wrinkle of the superficial skin at the wound surrounded by the opening or the cavity, so that the damage done to the wound by the movement-incurred wrinkle is prevented, and the damage done to the wound by the relative movement friction between the wound and the dressing without an opening in the conventional technology is prevented.

3. The opening or cavity of the protecting and fixing layer with the opening is configured to protect the wound. So even if the protecting and fixing layer is made by a non-transparent materials, as along as a transparent and detachable closing and opening member is disposed on the upper plane of the opening, the skin will not be hurt when opening, closing or changing the closing and opening member. With such configuration, the wound can be observed any time conveniently, and treated instantly without changing the whole device so that the damage done to the wound by moving the catheter and ripping the skin during changing the device is prevented and the cost is reduced.

4. Through adjusting the thickness of the protecting and fixing layer with the opening, or the height or volume of the cavity, the distance or level of contact between the dressing on the wound or the protecting and fixing layer with a pad and the surface of the wound can be configured so as to prevent conglutination and obstruction of blood circulation and supply caused by the dressing directly and tightly contacting and pressing the wound. It is also possible to configure an absorbing dressing on a wound surface with relatively large amount of secretion as a permeating and absorbing contact surface, so as to make sure the dressing will not conglutinate with the wound tissue and cause further damages while the dressing can absorb the wound secretion.

5. Wound inflammation and infection caused by sweat accumulation under the thin film and the adhesive irritation, which happens when using transparent thin film (PU film) to directly bond and cover infusion wounds in the conventional clinical technologies, is avoided.

6. Through bonding, combining and using protecting and fixing layers with openings made of different materials, the advantages of each one can be kept while the disadvantages can be overcome. When the flexible protecting and fixing layer is bonded with the rigid protecting and fixing layer while partially overlapping the rigid protecting and fixing layer, and the boundary of the flexible protecting and fixing layer is always larger than the boundary of the rigid protecting and fixing layer, because only the flexible protecting and fixing layer is bonded to the skin as the boundary of the fixing layer, its advantage of flexibly conforming to the surface of the skin and being not likely to peel and fall off is kept. The middle portion of the flexible protecting and fixing layer is bonded with the rigid protecting and fixing layer, while the openings can be anywhere between the two layers. The openings on all the layers are aligned with each other, while the wound is in the openings and the catheter being fixed is covered and bonded to the skin. This configuration keeps the advantage of the rigid protecting and fixing layer of not generating movement-incurred wrinkles, and overcomes the problems of catheter displacement, skin wrinkles, wound wrinkles, and the relative displacement frictions between the wounds and the dressing covering the wound caused by movement-incurred wrinkles of the skin or the dragging of an external force when there is only a flexible protecting and fixing layer covering and adhering to the catheter or the skin, or when only the opening of the flexible protecting and fixing layer surrounds the wound. At the same time, the whole surface of the rigid protecting and fixing layer is covered by the flexible protecting and fixing layer or only bonded to a middle portion of an upper surface of the flexible protecting and fixing layer, so that the disadvantage of peeling and falling off easily because of sweat or an increase of wound tension when only the rigid protecting and fixing layer adheres to the skin, is overcome.

7. By combining and bonding protecting and fixing layers with openings of different material characteristics with wound dressing or protecting and fixing layers of different material characteristics provided by the conventional technology, the disadvantages of the wound dressings or protecting and fixing layers provided by the conventional technologies are overcome while the advantages thereof are kept.

For a skilled person in the art to better understand the technical solutions of the present application, further detailed descriptions of the present patent application will be presented below with the illustrations of the drawings and various embodiments.

Embodiment 1

Figure 2:
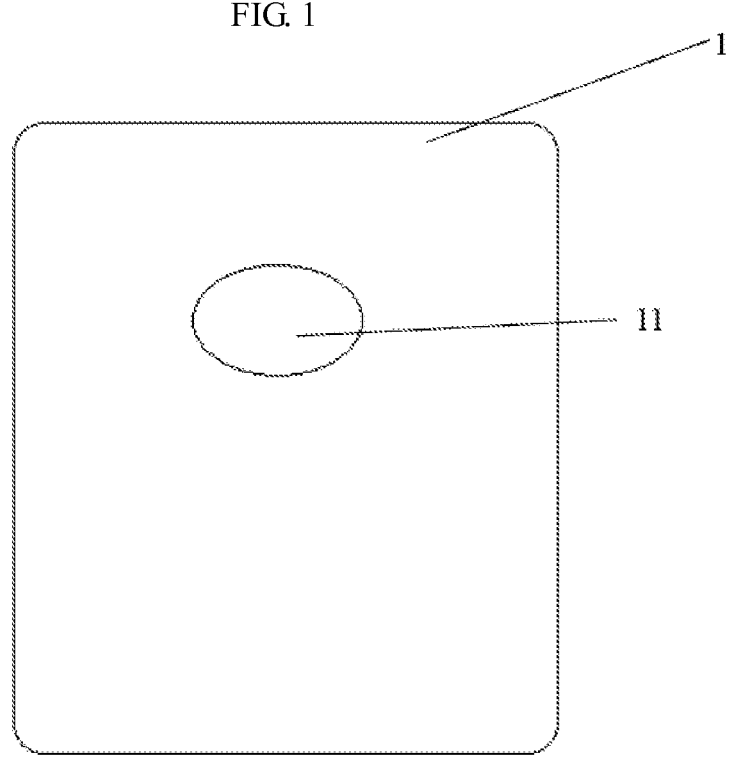
FIG. 2 is a diagram illustrating the structure of a flexible protecting and fixing layer with an opening.

Referring to FIG. 1 and FIG. 2, a wound protecting and fixing device in this embodiment includes a protecting and fixing layer 1 with an opening. An opening 11 is defined in the protecting and fixing layer 1 and configured to extend between an upper plane and a lower plane of the protecting and fixing layer 1 along a longitudinal direction. The area of the opening 11 is compatible with the area of the wound or the infusion wound so that the wound or the infusion wound is surrounded by the opening 11 so as to limit an increase of tension at the wound, to prevent the wound from being ripped and ruptured, and to limit a movement-incurred wrinkle of the skin at the wound and/or the opening of the wound.

An adhesive layer may be disposed at a lower surface of the protecting and fixing layer with the opening, or the protecting and fixing layer may be covered and bonded with a dressing made by conventional technologies (such as a non-woven dressing with a pad or transparent thin film) and thereby fixed to the skin around the wound. In this embodiment, the protecting and fixing layer with the opening is relatively thick.

In another embodiment, the protecting and fixing layer with the opening includes a flexible protecting and fixing layer with an opening and a rigid protecting and fixing layer with an opening. The flexible protecting and fixing layer with the opening may be a transparent thin film (PU film) and ultra-thin. Referring to FIG. 2, the flexible protecting and fixing layer with the opening is configured to tightly contact the skin, the object to be fixed, and the rigid protecting and fixing layer with the opening and not to fall off easily. The rigid protecting and fixing layer with the opening may be made of plastic, silicon gel, thickened non-woven cloth, foam, and hydrocolloid, and generally relatively thick, referring to FIG. 1. Generally, the rigid protecting and fixing layer with the opening is relatively thick, while the opening forms a cavity with a certain height and volume so as to limit an increase of tension at the wound surrounded by the opening or the cavity and a movement-incurred wrinkle of the superficial skin, prevent wound rips and ruptures, prevent damages from being done to the wound by the movement-incurred wrinkles of the wound superficial skin and the displacement of the catheter being fixed, and prevent damages from being done to the wound by the relative displacement frictions between the wound and the dressing. In addition, through adjusting the thickness of the protecting and fixing layer with the opening, or the height or volume of the cavity, the distance or level of contact between the dressing on the wound or the protecting and fixing layer with a pad and the surface of the wound can be configured so as to avoid conglutination and obstructions of blood circulation and supply caused by the dressing directly and tightly contacting and pressing the surface of the wound. It is also possible to configure an absorbing dressing on a wound surface with relatively a large amount of secretion as a permeating and absorbing contact surface, so as to make sure the dressing will not conglutinate with the wound tissue and cause further damages while the dressing can absorb the wound secretion.

In this embodiment, the opening of the protecting and fixing layer with the opening is configured to protect the wound. So even if the protecting and fixing layer is made by a non-transparent material, as along as a transparent and detachable closing and opening member is disposed on the upper plane of the opening, the skin will not be hurt when opening, closing or changing the closing and opening member. With such configuration, the wound can be observed any time conveniently, and treated instantly without changing the whole device so that the damage done to the wound by moving the catheter and ripping the skin during changing the device is prevented and the cost is reduced. Wound inflammation and infection caused by sweat accumulation under the thin film and the adhesive irritation, which happens when using transparent thin film (PU film) to directly bond and cover infusion wounds clinically in the conventional technology, is avoided.

Embodiment 2

Figure 3:
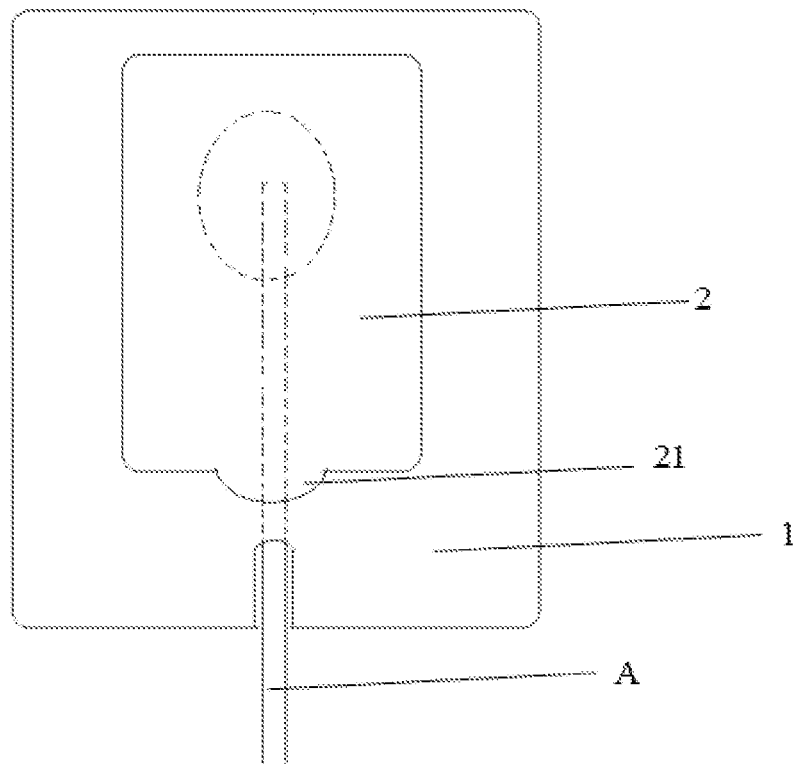
FIG. 3 is a perspective view of a wound protecting and fixing device in accordance with Embodiment 2 of the present patent application.
Figure 4:
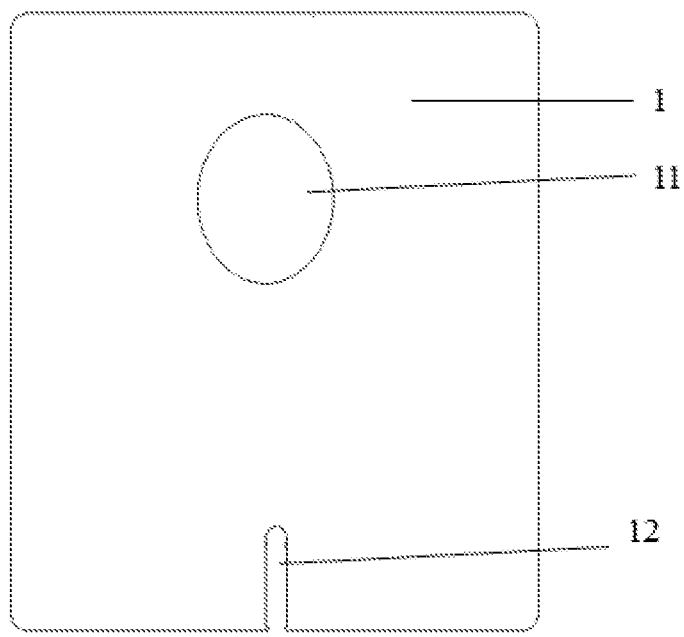
FIG. 4 is a diagram illustrating the structure of a protecting and fixing layer with an opening depicted in FIG. 3.

Referring to FIG. 3 and FIG. 4, a wound protecting and fixing device according to this embodiment includes a protecting and fixing layer with an opening 1 and a closing and opening member 2. The opening 11 of the protecting and fixing layer is aligned with the infusion wound while covering and bonding a catheter A onto the skin. The closing and opening member 2 is configured to seal the opening 11, so that the infusion wound is sealed and separated from the outside. A U shaped cut 12 is defined at an outer edge of the protecting and fixing layer with the opening, and configured to make the catheter being fixed be better conforming to the skin. The closing and opening member 2 is fixed with the protecting and fixing layer with the opening through an adhesive layer, which is disposed on a lower edge of the closing and opening member. Under an external force, the closing and opening member is partially or completely detached, so that a cavity 11 is exposed to the outside. The closing and opening member 2 includes a protruding wing 21 disposed at an edge thereof. The configuration of this protruding wing makes it convenient for a human hand or a mechanical tool to exert force to the closing and opening member. In operation, the human hand can work on this protruding wing, and thereby pull up and lay down the closing and opening member.

The protecting and fixing layer with the opening in this embodiment is made of an ultra-thin flexible material.

The closing and opening member 2 in this embodiment may be made of a transparent or non-transparent material. There is no adhesive in the area corresponding to the sealed cavity, so as to avoid infection caused by direct irritation made by the adhesive to the infusion wound. The protruding wing 21 is disposed at the edge of closing and opening member 2 so that the opening of the fixing layer can be sealed and opened any time conveniently, the infusion wound can be handled without changing the flexible protecting and fixing layer with the opening, and the damage to the infusion wound as well as skin irritation caused by moving the catheter during changing and peeling can be avoided. The operation of the embodiment is simple, while the frequency of changing the dressing is reduced and the cost is saved.

The catheter in this embodiment includes central venous catheters (CVC), peripherally inserted central catheters (PICC), vein retaining needle catheters, drainage tubes and etc.

Embodiment 3

Figure 5:
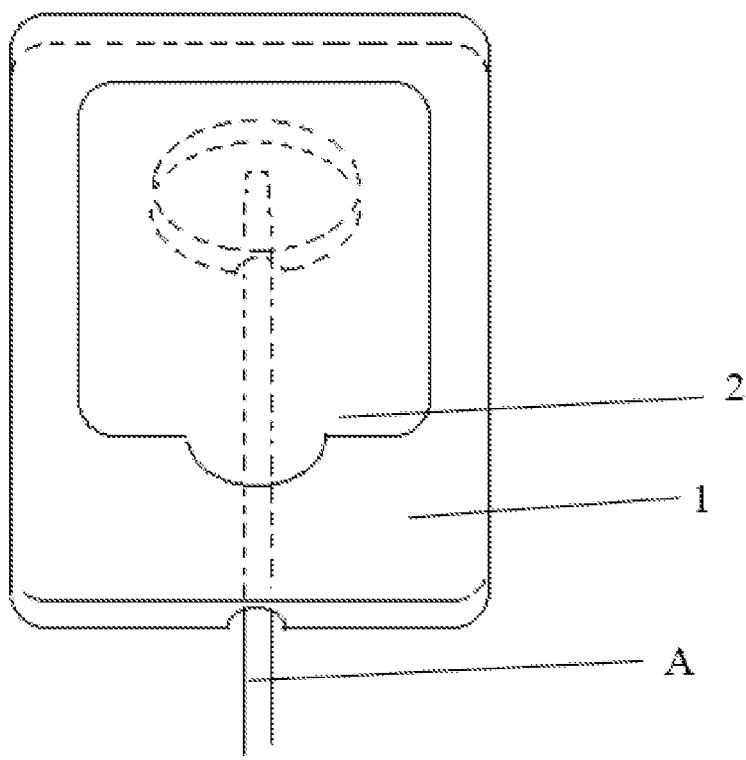
FIG. 5 is a perspective view of a wound protecting and fixing device in accordance with Embodiment 3 of the present patent application.
Figure 6:
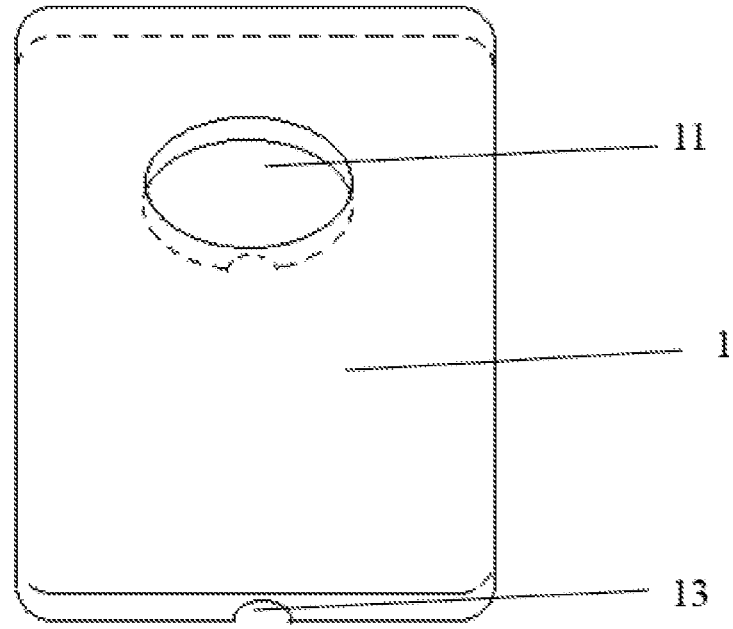
FIG. 6 is a diagram illustrating the structure of a protecting and fixing layer with an opening depicted in FIG. 5.

Referring to FIG. 5 and FIG. 6, the difference between this embodiment and Embodiment 2 is that the protecting and fixing layer with the opening 1 is made of a rigid material such as plastic, silicon gel, foam, hydrocolloid, thickened non-woven cloth and so on, and is relatively thick, which makes the opening 11 have a clear height and form a cavity. A passage 13 connecting the cavity to the outside is defined in the protecting and fixing layer with the opening 1. A catheter A is disposed in the passage 13, and fixed to the skin through an adhesive layer at a lower surface of the protecting and fixing layer with the opening 1. The opening 11 surrounds the infusion wound and a closing and opening member 2 seals the opening from the top.

The opening 11 in this embodiment can surround the wound so that the surface of the wound and the skin around the wound are surrounded by the edge of the cavity 11, thereby wound ripping and rupturing can be effectively prevented, the substantial part of the rigid protecting and fixing layer with the opening can be prevented from contacting the surface of the wound directly, and the wound is in a cavity formed by the opening where no object can touch. The rigid protecting and fixing layer with the opening is configured to limit the movement-incurred wrinkles of the superficial skin of the wound in the opening 11 or the cavity, so as to better protect the wound and eliminate contact and frictions with foreign objects and contact inflammation responses. The closing and opening member 2 is made of a transparent material so as to make it convenient to observe the wound situation and handle the wound any time without changing the whole device.

Embodiment 4

Figure 7:
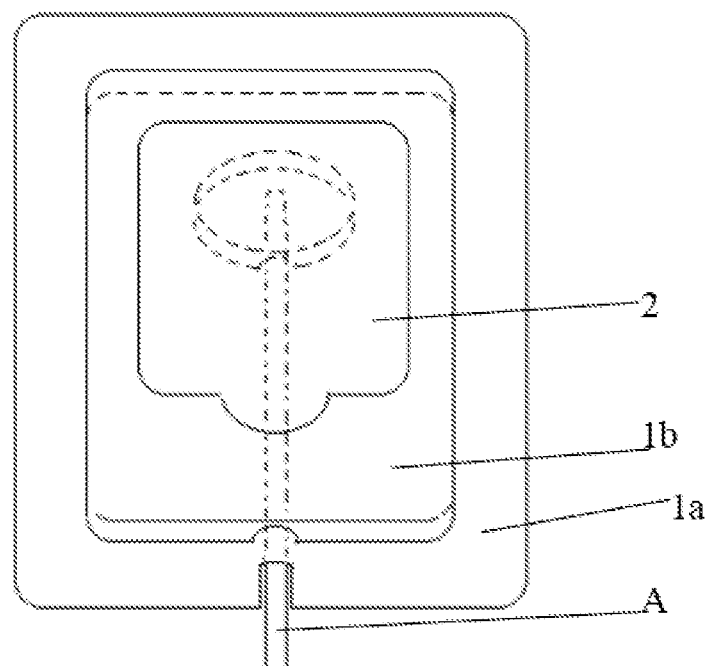
FIG. 7 is a perspective view of a wound protecting and fixing device in accordance with Embodiment 4 of the present patent application.

Referring to FIG. 7, being different from the above embodiments, in this embodiment, the wound protecting and fixing device includes a protecting and fixing layer with an opening and an closing and opening member, wherein the protecting and fixing layer with the opening includes a flexible protecting and fixing layer with an opening 1a, a rigid protecting and fixing layer with an opening 1b, and a closing and opening member 2. Through cooperatively using the flexible protecting and fixing layer with the opening 1a and the rigid protecting and fixing layer with the opening 1b, the infusion wound is protected and fixed and the catheter is fixed. The opening of the flexible protecting and fixing layer 1a is aligned with the infusion wound, and then the catheter A is covered and bonded to the skin around the wound so that the catheter A is fixed and the infusion wound is surrounded by the flexible protecting and fixing layer 1a. The rigid protecting and fixing layer with the opening 1b is bonded and fixed to an upper surface of the flexible protecting and fixing layer with the opening 1a, while the boundary of the flexible protecting and fixing layer with the opening 1a is larger than the boundary of the rigid protecting and fixing layer with the opening 1b. Therefore, for the whole device, only the flexible protecting and fixing layer 1a is bonded to the skin, the catheter A is bonded and fixed between the skin and the flexible protecting and fixing layer with the opening, the infusion wound is in the opening or cavity formed by the two protecting and fixing layers, and the closing and opening member seals the opening or cavity.

In this embodiment, because the flexible protecting and fixing layer with the opening 1a and the rigid protecting and fixing layer with the opening 1b are cooperatively used to protect and fix infusion wounds or regular wounds and prevent wound rupturing, the respective advantages of the flexible protecting and fixing layer with the opening 1a and the rigid protecting and fixing layer with the opening 1b are utilized while the disadvantages thereof are overcome, the catheter fixture is more secure, the protection of infusion wound is more effective, the time period for the device to be used for once is longer, the number of times of changing the device is fewer, and the cost is saved.

In this embodiment, the flexible protecting and fixing layer with the opening 1a is bonded with the rigid protecting and fixing layer with the opening 1b while not completely overlapping the rigid protecting and fixing layer with the opening 1b, and the boundary of the flexible protecting and fixing layer with the opening 1a is always larger than the boundary of the rigid protecting and fixing layer with the opening 1b. Because only the flexible protecting and fixing layer is bonded to the skin as the boundary of the fixing layer, the flexible protecting and fixing layer flexibly conforms to the surface of the skin and does not easily peel and fall off. The middle portion of the flexible protecting and fixing layer with the opening 1a is bonded with the rigid protecting and fixing layer with the opening 1b, while the infusion wound is in the cavity jointly formed by the two layers, and the catheter being fixed is covered and bonded to the skin. This configuration keeps the advantage of the rigid protecting and fixing layer of not generating movement-incurred wrinkles, and overcomes the problems of catheter A's displacement, skin wrinkles, wound wrinkles, and the relative displacement frictions between the wound and the dressing covering the wound, caused by movement-incurred wrinkles of the skin or the dragging of an external force, when there is only a flexible protecting and fixing layer with the opening 1a covering and adhering to the catheter A or the skin, or when only the opening of the flexible protecting and fixing layer 1a surrounds the wound, so that the infusion wound is not damaged thereby. At the same time, the whole surface of the rigid protecting and fixing layer with the opening 1b is bonded to a middle portion of an upper surface of the flexible protecting and fixing layer with the opening 1a, so that the disadvantage of peeling and falling off easily because of sweat or wound tension when only the rigid protecting and fixing layer with the opening 1b adheres to the skin is overcome.

Embodiment 5

Figure 8:
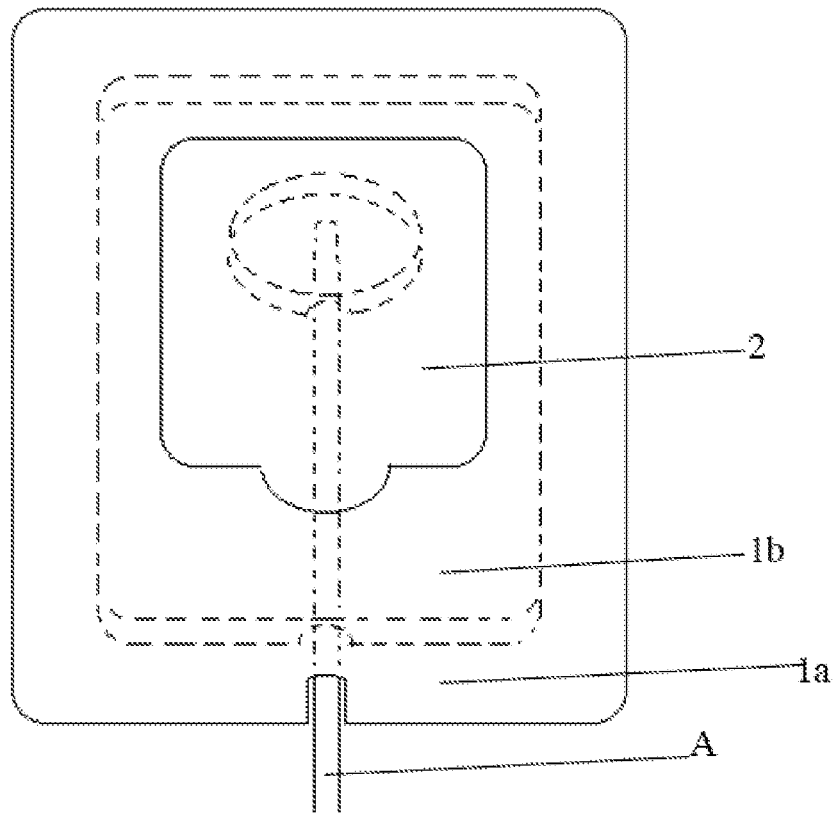
FIG. 8 is a perspective view of a wound protecting and fixing device in accordance with Embodiment 5 of the present patent application.

Referring to FIG. 8, the difference between this embodiment and Embodiment 4 is that the flexible protecting and fixing layer with the opening and the rigid protecting and fixing layer with the opening exchanges their positions so that the flexible protecting and fixing layer with the opening 1a is disposed at an upper position while the rigid protecting and fixing layer with the opening 1b is disposed under the flexible protecting and fixing layer with the opening 1a. The closing and opening member 2 seals the opening of the flexible protecting and fixing layer with the opening 1a. Such structure and configuration enhance the waterproof function.

Embodiment 6

Figure 9:
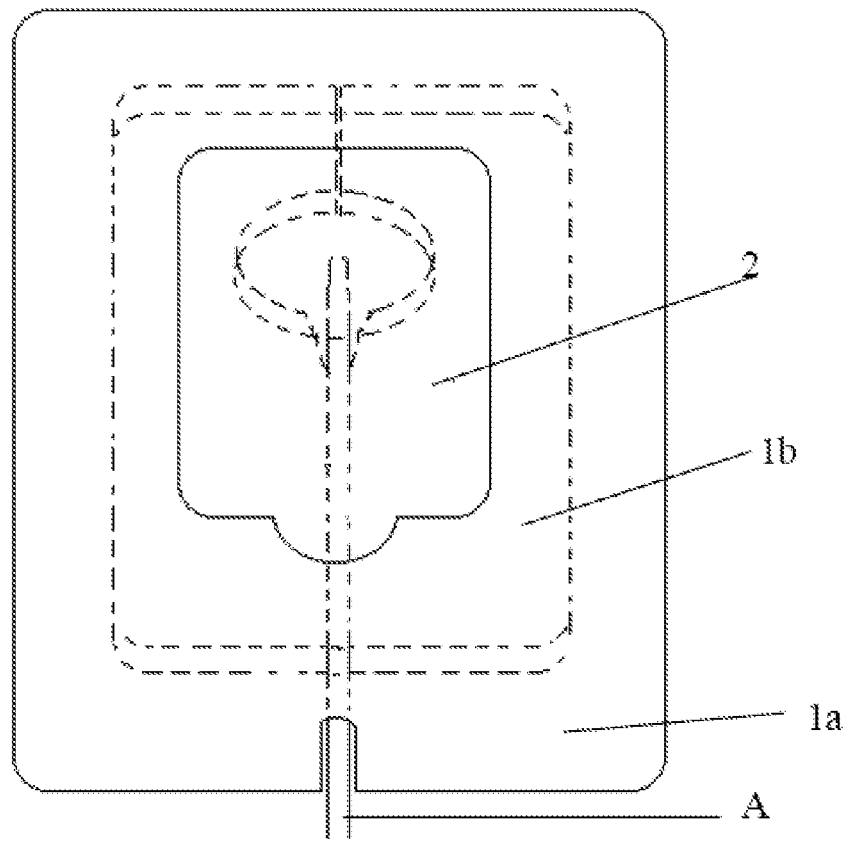
FIG. 9 is a perspective view of a wound protecting and fixing device in accordance with Embodiment 6 of the present patent application.
Figure 10:
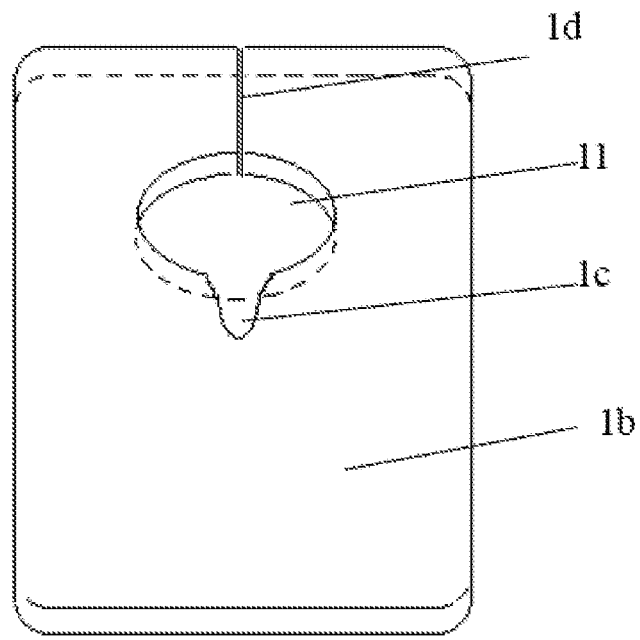
FIG. 10 is a diagram illustrating the structure of a rigid protecting and fixing layer with an opening having a groove and a slit as depicted in FIG. 9.

Referring to FIG. 9 and FIG. 10, the difference between this embodiment and Embodiment 4 is that a groove 1c is disposed at the surface of the edge of the opening of the rigid protecting and fixing layer 1b with the opening. The groove 1c is configured to facilitate the placement of the catheter. In addition, a through slit 1d is disposed between the boundary of the rigid protecting and fixing layer 1b with the opening and the opening. Through the slit 1d, the rigid protecting and fixing layer 1b with the opening surrounds the infusion wound between the skin and the catheter, so that the infusion wound is in the cavity formed by the opening, and the catheter is disposed on the rigid protecting and fixing layer 1b with the opening through the groove, thereby avoiding damages from being done by the catheter pressing the skin for a long time, especially for children's skin.

In this embodiment, the rigid protecting and fixing layer with the opening 1b works as a supporting pad of the catheter. The flexible protecting and fixing layer with the opening 1a covers and bonds the catheter and the rigid protecting and fixing layer with the opening 1b. The boundary of the flexible protecting and fixing layer 1a with the opening extends and adheres to the surface of the skin thereby fixing the whole device securely. The opening is sealed by the closing and opening member 2 from the top. Such configuration also enhances the waterproof function while the other functions are the same as in Embodiment 4.

Embodiment 7

Figure 11:
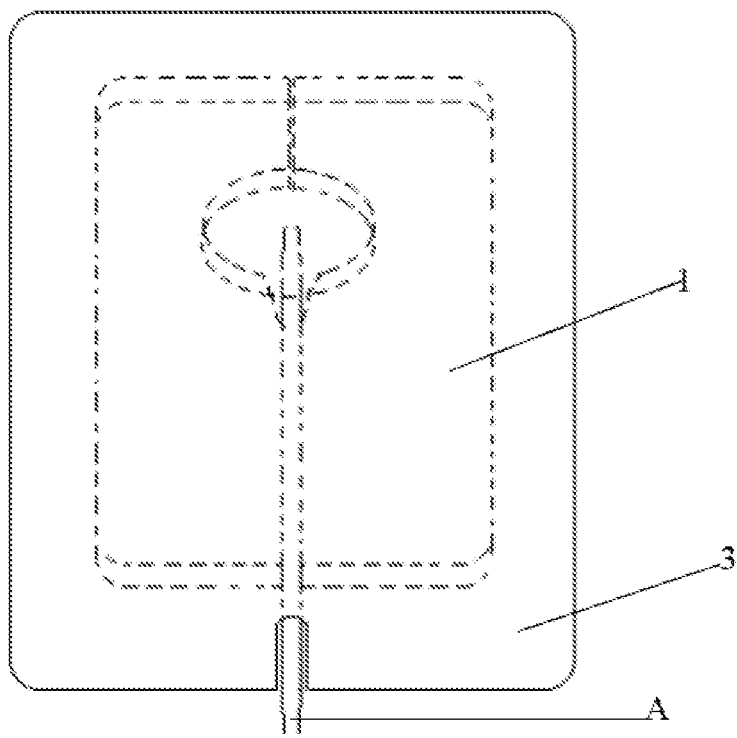
FIG. 11 is a perspective view of a wound protecting and fixing device in accordance with Embodiment 7 of the present patent application.

Referring to FIG. 11, in this embodiment, the wound protecting and fixing device includes a rigid protecting and fixing layer 1 with an opening and a flexible protecting and fixing layer 3 without an opening. This embodiment is mainly used for short term protection and fixing of infusion wounds, and requires changing the whole device when being changed, the advantage of which is strong waterproof capability. The other functions are the same as in Embodiment 6.

Embodiment 8

Figure 12:
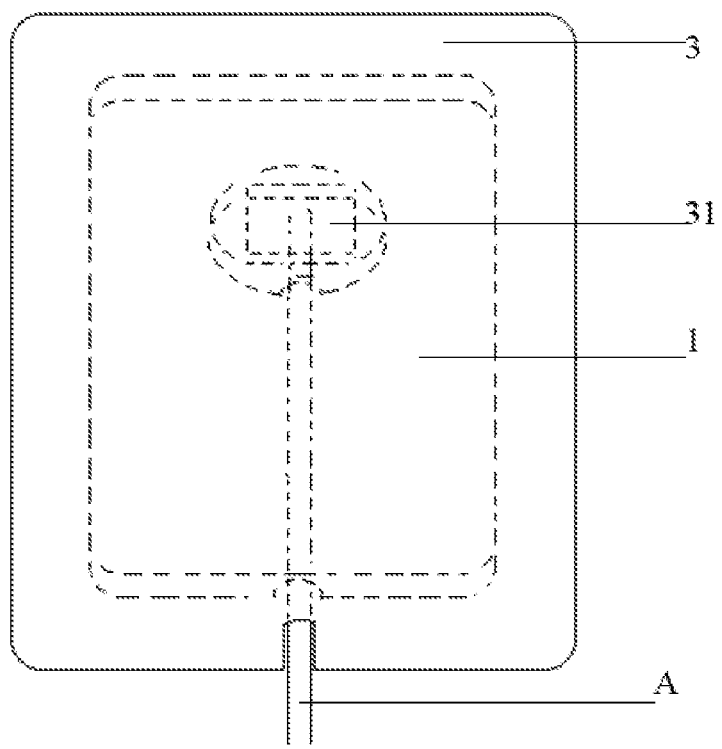
FIG. 12 is a perspective view of a wound protecting and fixing device in accordance with Embodiment 8 of the present patent application.
Figure 13:
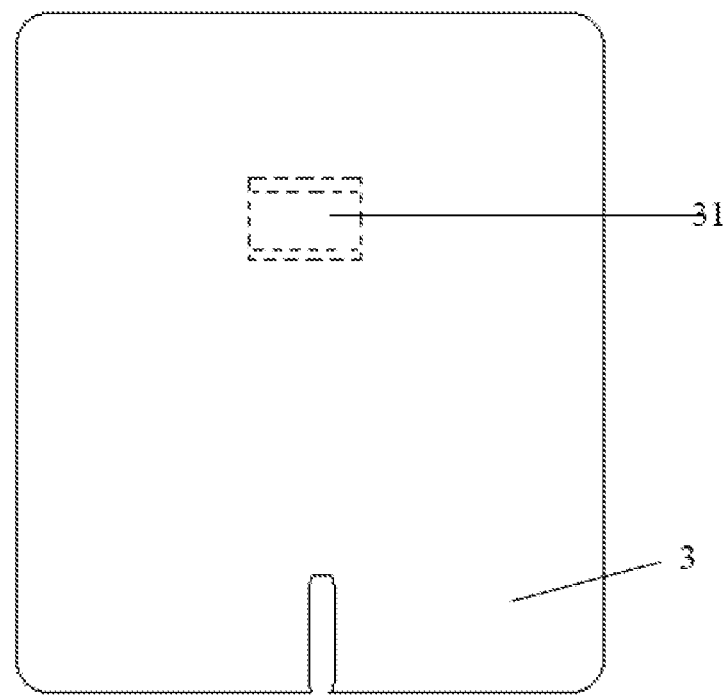
FIG. 13 is a diagram illustrating the structure of a flexible protecting and fixing layer with an opening having a pad as depicted in FIG. 12.

Referring to FIG. 12 and FIG. 13, the difference between this embodiment and Embodiment 7 is that in this embodiment, the flexible protecting and fixing layer 3 includes a pad 31. Through the pad 31 absorbing oozed liquid and leaked blood of the infusion wounds, the device is applicable to infusion wounds that are recently established. The other functions are the same as in Embodiment 7.

Embodiment 9

Figure 14:
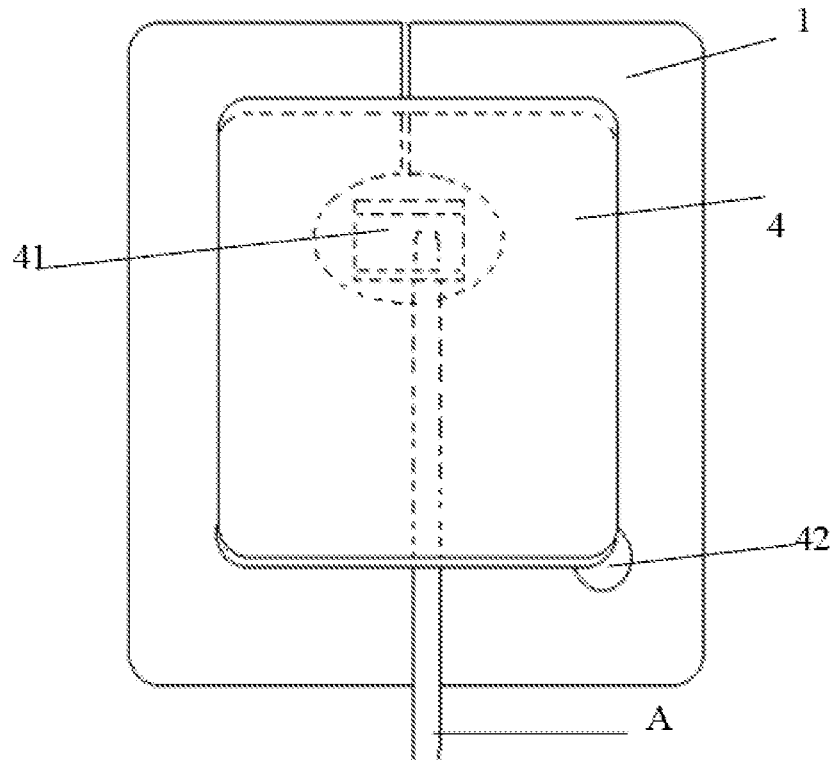
FIG. 14 is a perspective view of a wound protecting and fixing device in accordance with Embodiment 9 of the present patent application.
Figure 15:
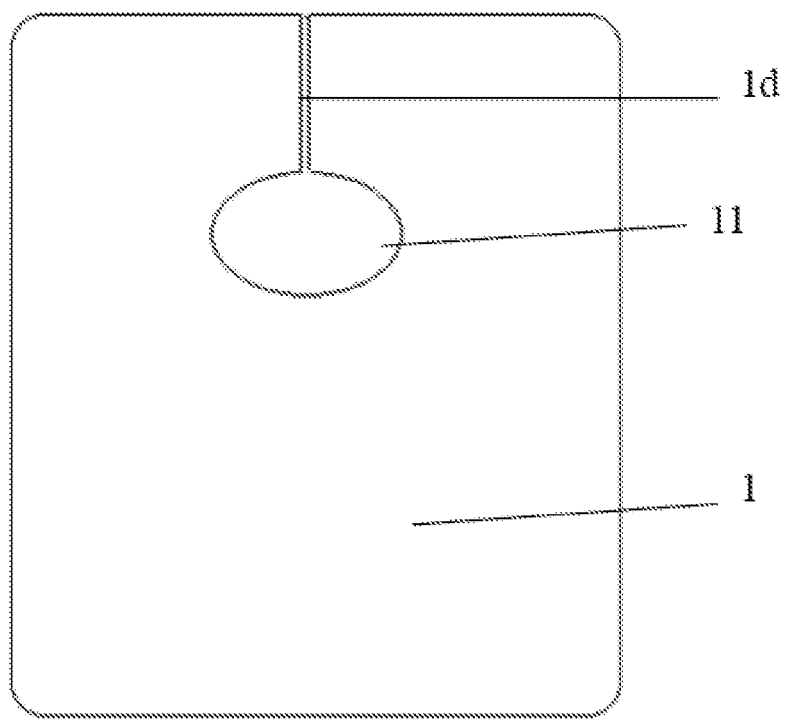
FIG. 15 is a diagram illustrating the structure of a protecting and fixing layer with an opening depicted in FIG. 14.
Figure 16:
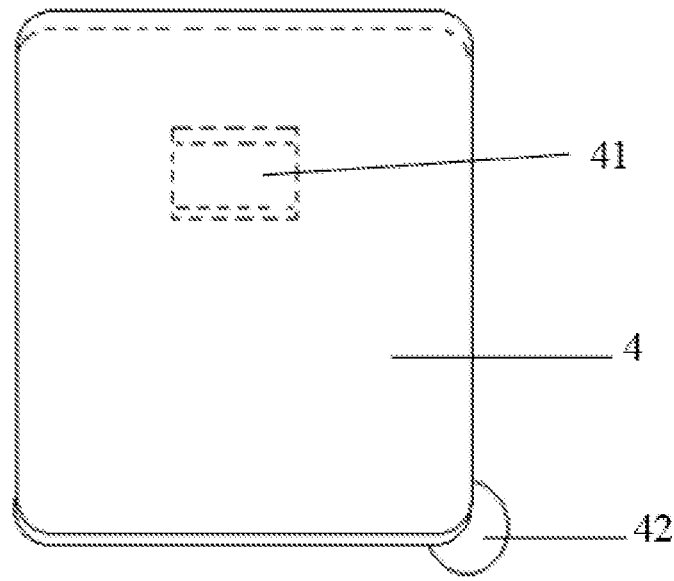
FIG. 16 is a diagram illustrating the structure of a rigid protecting and fixing layer with an opening having a pad depicted in FIG. 14.

Referring to FIG. 14, FIG. 15 and FIG. 16, a wound protecting and fixing device according to this embodiment includes a flexible protecting and fixing layer 1 with an opening and a rigid protecting and fixing layer 4 with a pad. The pad 41 is included in the rigid protecting and fixing layer 4 and disposed at a lower portion thereof. A slit 1d is defined between the opening 11 of the protecting and fixing layer 1 and an edge thereof. The opening 11 of the protecting and fixing layer 1 surrounds the infusion wound, and the protecting and fixing layer 1 adheres to the skin. The catheter is disposed on an upper surface of the protecting and fixing layer 1. The rigid protecting and fixing layer 4 with the pad covers and bonds the catheter to the upper surface of the protecting and fixing layer 1 so as to fix the catheter. In this embodiment, because the rigid protecting and fixing layer 4 with the pad adheres to the top of the protecting and fixing layer 1, it is more securely fixed than the case in the conventional technology where only the rigid protecting and fixing layer 4 is used. The pad 41 of the rigid protecting and fixing layer 4 with the pad is configured to absorb the oozed liquid of the wound and mainly used for protecting infusion wound that has recently been punctured. A protruding wing 42 is disposed on a corner of an outer boundary of the rigid protecting and fixing layer 4, and configured for peeling off and changing the rigid protecting and fixing layer. In this embodiment, the rigid protecting and fixing layer 4 is not transparent, but is air permissive and capable of absorbing oozed liquid so that infection caused by sweat accumulation at the wound in the case where only a transparent thin film is used for protection and fixing is avoided. This embodiment is mainly applicable to protecting newly established and short-term infusion wounds, and fixing the catheter in those cases.

Embodiment 10

Figure 17:
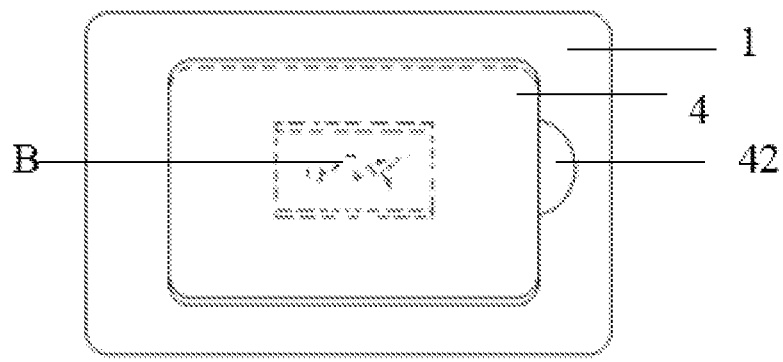
FIG. 17 is a structural view of a wound protecting and fixing device in accordance with Embodiment 10 of the present patent application.
Figure 18:
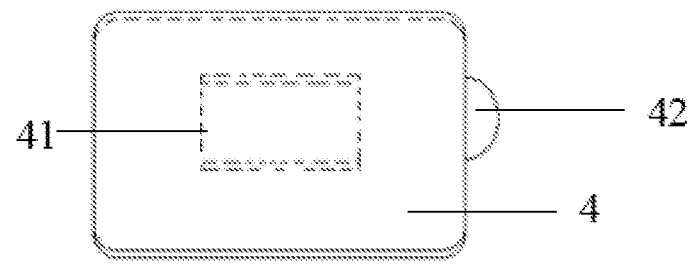
FIG. 18 is a diagram illustrating the structure of a rigid protecting and fixing layer with an opening having a pad and a protruding wing depicted in FIG. 17.
Figure 19:
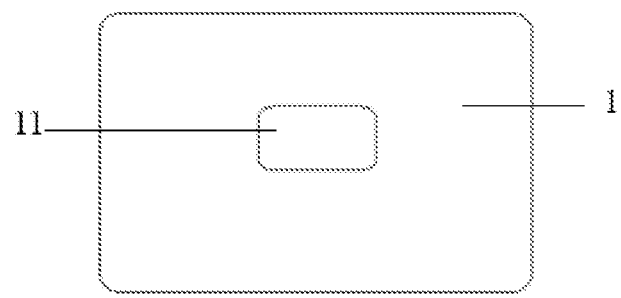
FIG. 19 is a diagram illustrating the structure of a protecting and fixing layer with an opening depicted in FIG. 17.

Referring to FIG. 17, FIG. 18 and FIG. 19, a wound protecting and fixing device according to this embodiment includes a protecting and fixing layer 1 with an opening made of a flexible material and a rigid protecting and fixing layer 4 with a pad. The opening 11 of the flexible protecting and fixing layer 1 is aligned with a wound B and adhering to the skin around the wound B. The rigid protecting and fixing layer 4 with a pad is then covered onto the wound and bonded with the protecting and fixing layer 1 with the opening. In this embodiment, the protecting and fixing layer 1 enhances the fixing security of the rigid protecting and fixing layer 4 and the embodiment is especially applicable to wounds at the movable joint parts. Skin wrinkles caused by any movement will not make the wound protecting and fixing device be detached and fall off from the skin. A protruding wing 42 is disposed at an edge of the rigid protecting and fixing layer 4 and configured to make it convenient to peel off the rigid protecting and fixing layer 4 and change the rigid protecting and fixing layer 4, while keeping the flexible protecting and fixing layer 1a with the opening unchanged at the same time.

Embodiment 11

Figure 20:
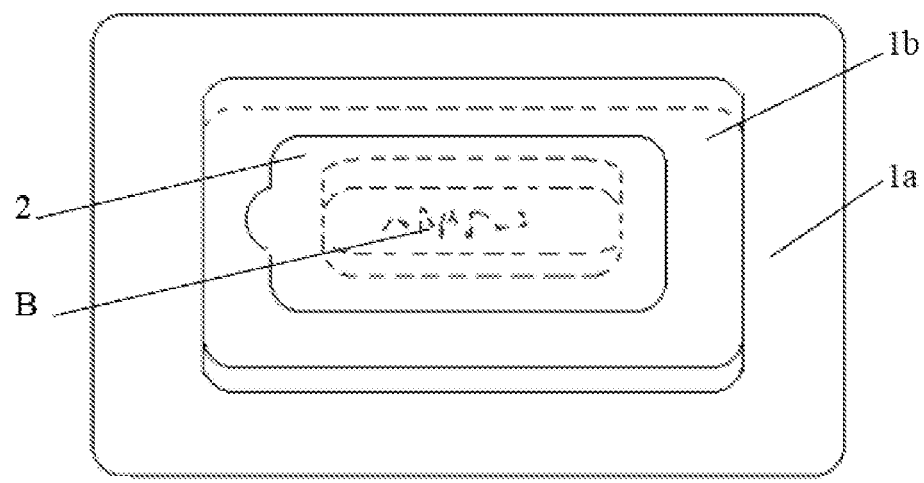
FIG. 20 is a structural view of a wound protecting and fixing device in accordance with Embodiment 11 of the present patent application.
Figure 21:
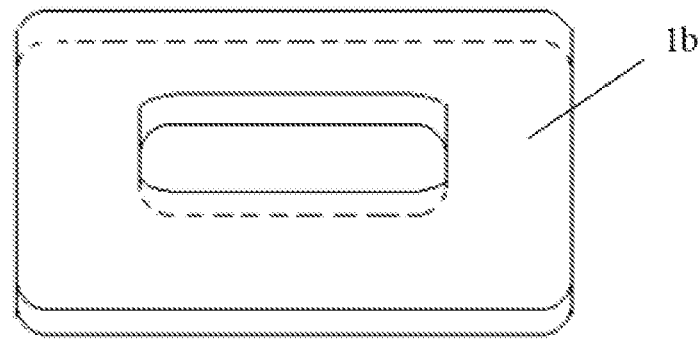
FIG. 21 is a diagram illustrating the structure of a rigid protecting and fixing layer with an opening depicted in FIG. 20.
Figure 22:
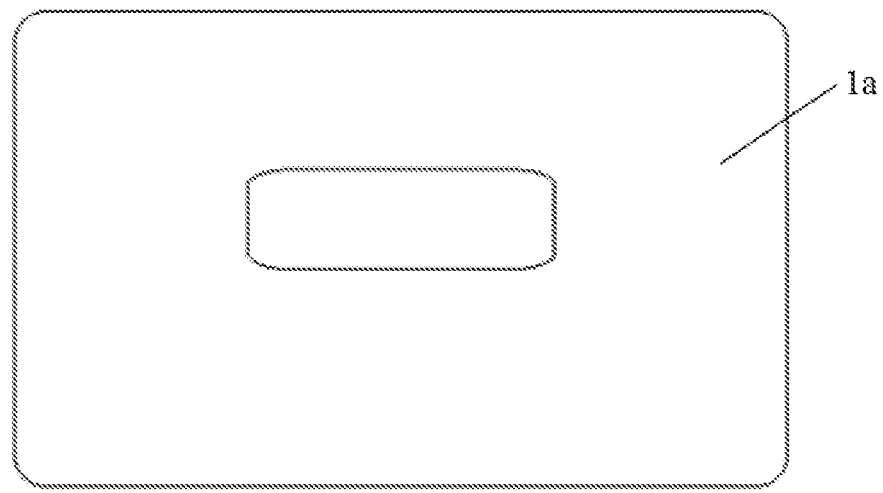
FIG. 22 is a diagram illustrating the structure of a flexible protecting and fixing layer with an opening depicted in FIG. 20.

Referring to FIG. 20, FIG. 21 and FIG. 22, a wound protecting and fixing device according to this embodiment includes a protecting and fixing layer with an opening and a closing and opening member 2. The protecting and fixing layer with the opening includes a flexible protecting and fixing layer with an opening 1a and a rigid protecting and fixing layer with an opening 1b. In this embodiment, the opening of the rigid protecting and fixing layer 1b accommodates a wound B, limits the increase of tension of the wound B, prevents the wound B from being ripped and ruptured, limits the wound damage caused by movement-incurred wrinkles of the superficial skin of the wound B, prevents blood circulation obstruction and inflammatory responses due to foreign object contact caused by a foreign object tightly pressing and contacting the wound B. Through the transparent closing and opening member 2, the healing situation of the wound B can be monitored any time, while debriding, sanitization, drainage, and regional medical and physical treatment may be conducted to the wound B without changing the whole protecting and fixing device.

Embodiment 12

Figure 23:
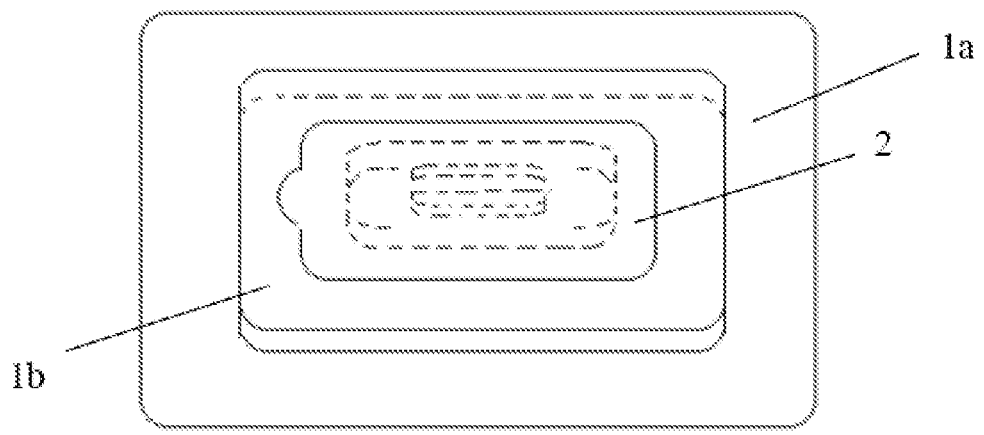
FIG. 23 is a perspective view of a wound protecting and fixing device in accordance with Embodiment 12 of the present patent application.
Figure 24:
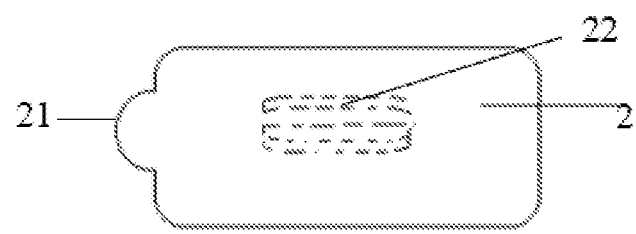
FIG. 24 is a diagram illustrating a closing and opening member with a pad as depicted in FIG. 23.

Referring to FIG. 23 and FIG. 24, the difference between this embodiment and Embodiment 11 is that a pad 22 is disposed under a lower surface of the closing and opening member 2. The pad 22 has functions such as strong absorption and antibiosis capabilities. Through adjusting the height or volume of the cavity of the rigid protecting and fixing layer 1b with the opening, the distance or level of contact between the pad 22 in the cavity above the wound and the surface of the wound can be configured so as to avoid conglutination and blood circulation and supply obstructions caused by the pad 22 directly and tightly contacting and pressing the surface of the wound. It is also possible to configure the pad 22 to be a permeating and absorbing contact surface to the wound surface, so as to make sure the pad 22 will not conglutinate with the wound tissue and cause further damages while the pad 22 can absorb the wound secretion. In this embodiment, the pad 22 disposed under the closing and opening member 2 is also suitable for protecting and fixing infusion wounds and having the same functions. The other functions are the same as in Embodiment 11.

Embodiment 13

Figure 25:
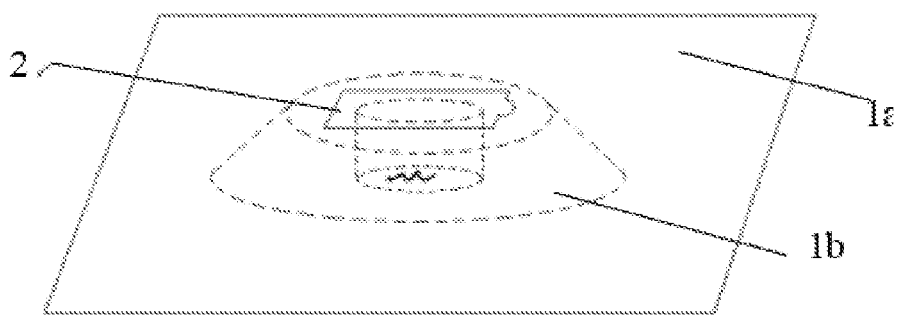
FIG. 25 is a perspective view of a wound protecting and fixing device in accordance with Embodiment 13 of the present patent application.

Referring to FIG. 25, in this embodiment a wound protecting and fixing device includes a protecting and fixing layer with an opening. The protecting and fixing layer with the opening includes a flexible protecting and fixing layer 1a with an opening, and a rigid protecting and fixing layer 1b with an opening below the flexible protecting and fixing layer 1a with the opening. The rigid protecting and fixing layer 1b with the opening has a shape of truncated cone. The flexible protecting and fixing layer 1a with the opening covers and adheres to the skin. A closing and opening member 2 is disposed at the opening. This configuration, besides keeping the functions that it should have, is mainly for making the flexible protecting and fixing layer with the opening conform to the skin surface and fixed to the wound skin well, while increasing the height of the cavity. At the same time, the area of the bottom of the rigid protecting and fixing layer with the opening is reduced and the material cost is saved.

Embodiment 14

Figure 26:
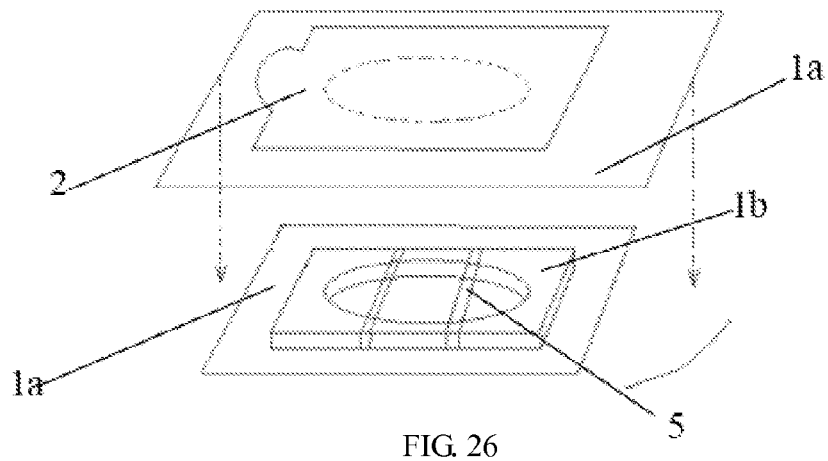
FIG. 26 is an exploded view of a wound protecting and fixing device in accordance with Embodiment 14 of the present patent application.

Referring to FIG. 26, in this embodiment a wound protecting and fixing device includes a protecting and fixing layer with an opening. The protecting and fixing layer with the opening includes two flexible protecting and fixing layers 1a with openings, a rigid protecting and fixing layer 1b with an opening, and an closing and opening member 2. A supporting member 5 is disposed on an upper portion of the rigid protecting and fixing layer 1b with the opening. The supporting member 5 has bar shape and is disposed above the rigid protecting and fixing layer 1b with the opening, extending to a side wall of the rigid protecting and fixing layer with the opening and being fixed thereto. The supporting member is made of a material that has certain rigidity and does not deform easily, such as silicon gel, PVC materials or other plastics. The purpose of setting up the supporting member is to enhance the fixture of the rigid protecting and fixing layer with the opening, and prevent the closing and opening member from collapsing and touching the wound. Especially for relatively large wound surface, setting up the supporting member is particularly necessary.

In above embodiments, the cavity in the rigid protecting and fixing layer with the opening is configured to connect the upper surface and the lower surface of the rigid protecting and fixing layer with the opening all the way through the rigid protecting and fixing layer with the opening. In practice, the cavity in the rigid protecting and fixing layer with the opening may be configured to only connect with the lower surface, thereby forming an opening on the lower surface, and not to connect with the upper surface so that there is no opening formed on the upper surface.

While the present patent application has been shown and described with particular references to a number of embodiments thereof, the descriptions made to the embodiments are intended to illustrate the method and the core idea of the present invention. It should be noted that various other improvements or modifications may be made without departing from the scope of the present invention, and these improvements and modifications are also in the scope of protection of the claims.

What is claimed is:

1. A wound protecting and fixing device comprising:
   at least a protecting and fixing layer with an opening; and
   a closing and opening member disposed at the protecting and fixing layer with the opening; wherein:
   the opening is defined in the protecting and fixing layer and configured to extend between an upper plane and a lower plane of the protecting and fixing layer along a longitudinal direction, and to surround a wound therein;
   the protecting and fixing layer with the opening comprises a flexible protecting and fixing layer with an opening and a rigid protecting and fixing layer with an opening, the flexible protecting and fixing layer having a planar shape,
   the rigid protecting and fixing layer having a planar shape and a rigidity greater than a rigidity of the flexible protecting and fixing layer,
   the rigid protecting and fixing layer being configured for limiting an increase of tension at the wound and a movement-incurred wrinkle of skin at the wound,
   a cavity being defined inside and extending through material of the rigid protecting and fixing layer and accommodating the wound, the cavity being embedded and confined within the material of the rigid protecting and fixing layer without extending beyond the material of the rigid protecting and fixing layer;
   the flexible protecting and fixing layer and the rigid protecting and fixing layer are bonded together and aligned by the openings; and
   the closing and opening member is configured to close or open the opening, and detachably fixed with the upper plane of the protecting and fixing layer with the opening through an adhesive layer.

2. The wound protecting and fixing device of claim 1 further comprising an adhesive layer, the adhesive layer being disposed on a surface of the protecting and fixing layer with the opening.

3. The wound protecting and fixing device of claim 1, wherein the flexible protecting and fixing layer is configured to follow a movement-incurred wrinkle of a texture of superficial skin that the flexible protecting and fixing layer adheres to and produce the same movement-incurred wrinkle, and the rigid protecting and fixing layer is configured to limit a movement-incurred wrinkle of the skin that the rigid protecting and fixing layer adheres to, a movement-incurred wrinkle of the flexible protecting and fixing layer, a wound rupture surrounded by the opening, and a movement-incurred wrinkle of superficial skin of the wound.

4. The wound protecting and fixing device of claim 1 further comprising a pad, the pad being disposed under a lower surface of the closing and opening member.

5. The wound protecting and fixing device of claim 1, wherein the closing and opening member comprises a protruding wing disposed at an edge thereof.

6. The wound protecting and fixing device of claim 1, wherein a passage connecting the cavity to the outside is defined in the rigid protecting and fixing layer with the opening, the passage being configured to allow an object to enter or exit the cavity.

7. The wound protecting and fixing device of claim 1, wherein a longitudinal cross-section of the rigid protecting and fixing layer with the opening has a trapezoid shape.

8. The wound protecting and fixing device of claim 1, wherein the flexible protecting and fixing layer with the opening is disposed below or above the rigid protecting and fixing layer with the opening, an outer boundary of the flexible protecting and fixing layer with the opening being extending beyond an outer boundary of the rigid protecting and fixing layer with the opening.

9. The wound protecting and fixing device of claim 1, wherein a U shaped cut is defined at an outer edge of the protecting and fixing layer with the opening.

10. The wound protecting and fixing device of claim 1 further comprising a supporting member, the supporting member being fixed with at least an upper portion of the protecting and fixing layer with the opening.

11. The wound protecting and fixing device of claim 10, wherein the supporting member is a supporting bar, a supporting chip, a supporting block, or a supporting frame.

12. The wound protecting and fixing device of claim 1, wherein the protecting and fixing layer with the opening is a combination of multiple layers of different materials.

13. The wound protecting and fixing device of claim 1, wherein an outer edge of the protecting and fixing layer with the opening is connected to the opening through a slit.

14. The wound protecting and fixing device of claim 1, wherein
   the flexible protecting and fixing layer has first and second surfaces opposite to each other,
   the first surface is undetachably bonded to the rigid protecting and fixing layer, and
   the second surface is detachably fixed to the closing and opening member.

15. The wound protecting and fixing device of claim 14, wherein the flexible protecting and fixing layer has a perimeter greater than a perimeter of the rigid protecting and fixing layer, and the flexible protecting and fixing layer and the rigid protecting and fixing layer are configured to directly contact the skin.

16. The wound protecting and fixing device of claim 15, wherein the rigid protecting and fixing layer has a thickness greater than a thickness of the flexible protecting and fixing layer.

17. The wound protecting and fixing device of claim 16, wherein the rigid protecting and fixing layer further comprises:
   a slit extending from a boundary of the rigid protecting and fixing layer to an edge of the opening of the rigid protecting and fixing layer, and
   a groove at the edge of the opening of the rigid protecting and fixing layer for inserting a catheter, and
   the flexible protecting and fixing layer further comprises a U-shaped cut at an outer edge of the flexible protecting and fixing layer, the U-shaped cut being aligned to the groove of the rigid protecting and fixing layer.

18. The wound protecting and fixing device of claim 14, wherein the flexible protecting and fixing layer has a perimeter greater than a perimeter of the rigid protecting and fixing layer, and
   the rigid protecting and fixing layer has a thickness greater than a thickness of the flexible protecting and fixing layer.

19. The wound protecting and fixing device of claim 18, further comprising another flexible protecting and fixing layer with an opening, wherein said another flexible protecting and fixing layer is bonded to the rigid protecting and fixing layer on a side opposite to a side bonded with the flexible protecting and fixing layer, and configured to directly contact the skin.

20. The wound protecting and fixing device of claim 19, further comprising a supporting member disposed between the flexible protecting and fixing layer and the rigid protecting and fixing layer, and extending from one sidewall of the rigid protecting and fixing layer to another sidewall of the rigid protecting and fixing layer.

* * * * *